(12) United States Patent
Chattaraj et al.

(10) Patent No.: US 10,589,038 B2
(45) Date of Patent: Mar. 17, 2020

(54) SET CONNECTOR SYSTEMS FOR VENTING A FLUID RESERVOIR

(71) Applicant: MEDTRONIC MINIMED, INC., Northridge, CA (US)

(72) Inventors: Sarnath Chattaraj, Simi Valley, CA (US); Kiem H. Dang, Thousand Oaks, CA (US); Poonam S. Gulati, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 480 days.

(21) Appl. No.: 15/140,229

(22) Filed: Apr. 27, 2016

(65) Prior Publication Data
US 2017/0312454 A1    Nov. 2, 2017

(51) Int. Cl.
*A61M 5/36* (2006.01)
*A61M 5/168* (2006.01)
(Continued)

(52) U.S. Cl.
CPC .............. *A61M 5/36* (2013.01); *A61M 5/142* (2013.01); *A61M 5/14212* (2013.01);
(Continued)

(58) Field of Classification Search
CPC .......... A61M 5/38; A61M 5/385; A61M 5/36; A61M 5/14212; A61M 5/14244;
(Continued)

(56) References Cited

U.S. PATENT DOCUMENTS 3,631,654 A * 1/1972 Riely .................... A61M 5/165
                                                                    210/446
3,631,847 A    1/1972 Hobbs, II
(Continued)

FOREIGN PATENT DOCUMENTS

DE          4329229       3/1995
EP          0319268       11/1988
(Continued)

OTHER PUBLICATIONS

PCT Search Report (PCT/US02/03299), dated Oct. 31, 2002, Medtronic Minimed, Inc.
(Continued)

*Primary Examiner* — Jason E Flick
*Assistant Examiner* — Justin L Zamory
(74) *Attorney, Agent, or Firm* — Lorenz & Kopf, LLP

(57) ABSTRACT

A set connector system for venting a gas from a fluid reservoir of a fluid infusion device is provided. The set connector system includes a connector system having a first body section coupled to a second body section. The first body section defines a bore in communication with a chamber and a counterbore of the second body section to define a fluid flow path from the fluid reservoir. The chamber of the second body section is in fluid communication with a vent subsystem defined through the second body section. The vent subsystem terminates in an outlet, and the vent subsystem directs gas in the fluid flow path through the second body section to the outlet.

13 Claims, 12 Drawing Sheets

(51) Int. Cl.
  *A61M 5/142* (2006.01)
  *A61M 39/24* (2006.01)
  *A61M 39/10* (2006.01)

(52) U.S. Cl.
  CPC .... *A61M 5/14244* (2013.01); *A61M 5/16813* (2013.01); *A61M 39/10* (2013.01); *A61M 39/24* (2013.01); *A61M 2205/502* (2013.01); *A61M 2205/7527* (2013.01)

(58) Field of Classification Search
  CPC .. A61M 5/16813; A61M 5/142; A61M 39/24; A61M 39/10; A61M 39/1011; A61M 2205/502; A61M 2205/7527; A61M 2205/7536
  See application file for complete search history.

(56) References Cited

U.S. PATENT DOCUMENTS

| | | |
|---|---|---|
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,834,706 A * | 5/1989 | Beck .................. A61M 39/1011 604/111 |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |

(56) References Cited

U.S. PATENT DOCUMENTS

| | | |
|---|---|---|
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0092873 A1 | 5/2004 | Moberg |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0143714 A1* | 6/2005 | Hegland ............... A61M 39/12 604/533 |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0114308 A1* | 5/2008 | di Palma ............ A61M 39/0208 604/246 |
| 2008/0132849 A1* | 6/2008 | Horiguchi ........... A61M 1/3655 604/175 |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |
| 2012/0192968 A1 | 8/2012 | Bonnal et al. |
| 2013/0053816 A1 | 2/2013 | DiPerna et al. |
| 2013/0338588 A1 | 12/2013 | Grimm et al. |
| 2014/0246616 A1 | 9/2014 | Fangrow |
| 2015/0057613 A1 | 2/2015 | Clemente et al. |
| 2015/0190588 A1* | 7/2015 | Hanson ................ A61M 5/158 604/123 |
| 2016/0089505 A1* | 3/2016 | Alderete, Jr. ......... A61M 5/482 604/118 |
| 2016/0095987 A1 | 4/2016 | Chattaraj et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO 2006/052655 A2 | 5/2006 |

OTHER PUBLICATIONS (Animas Corporation, 1999). Animas . . . bringing new life to insulin therapy.

(56) References Cited

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998), MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

(56) References Cited

OTHER PUBLICATIONS

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

SET CONNECTOR SYSTEMS FOR VENTING A FLUID RESERVOIR

TECHNICAL FIELD

Embodiments of the subject matter described herein relate generally to fluid infusion devices for delivering a medication fluid to the body of a user. More particularly, embodiments of the subject matter relate to set connector systems for venting a gas from a fluid reservoir of a fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In many instances, the fluid reservoir requires filling by the patient prior to use in the external fluid infusion device. During the filling of the fluid reservoir, gas, such as air, may inadvertently become trapped in the fluid reservoir.

Accordingly, it is desirable to provide set connector systems for venting a gas, such as air, from a fluid reservoir for use with a fluid infusion device. Furthermore, other desirable features and characteristics will become apparent from the subsequent detailed description and the appended claims, taken in conjunction with the accompanying drawings and the foregoing technical field and background.

BRIEF SUMMARY

According to various embodiments, provided is a set connector system for venting a gas from a fluid reservoir of a fluid infusion device. The set connector system includes a connector system having a first body section coupled to a second body section. The first body section defines a bore in communication with a chamber and a counterbore of the second body section to define a fluid flow path from the fluid reservoir. The chamber of the second body section is in fluid communication with a vent subsystem defined through the second body section. The vent subsystem terminates in an outlet, and the vent subsystem directs gas in the fluid flow path through the second body section to the outlet.

Also provided according to various embodiments is a fluid infusion device. The fluid infusion device comprises a housing that receives a fluid reservoir, and a set connector system for venting a gas from the fluid reservoir. The set connector system includes a connector system having a first body section coupled to a second body section. The first body section defines a bore. The second body section includes a counterbore that receives a portion of the fluid reservoir. The bore of the first body section and the counterbore of the second body section cooperate to define a fluid flow path from the fluid reservoir. The second body section includes a vent subsystem in communication with the fluid flow path that terminates in an outlet, and the vent subsystem directs gas in the fluid flow path to the outlet.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
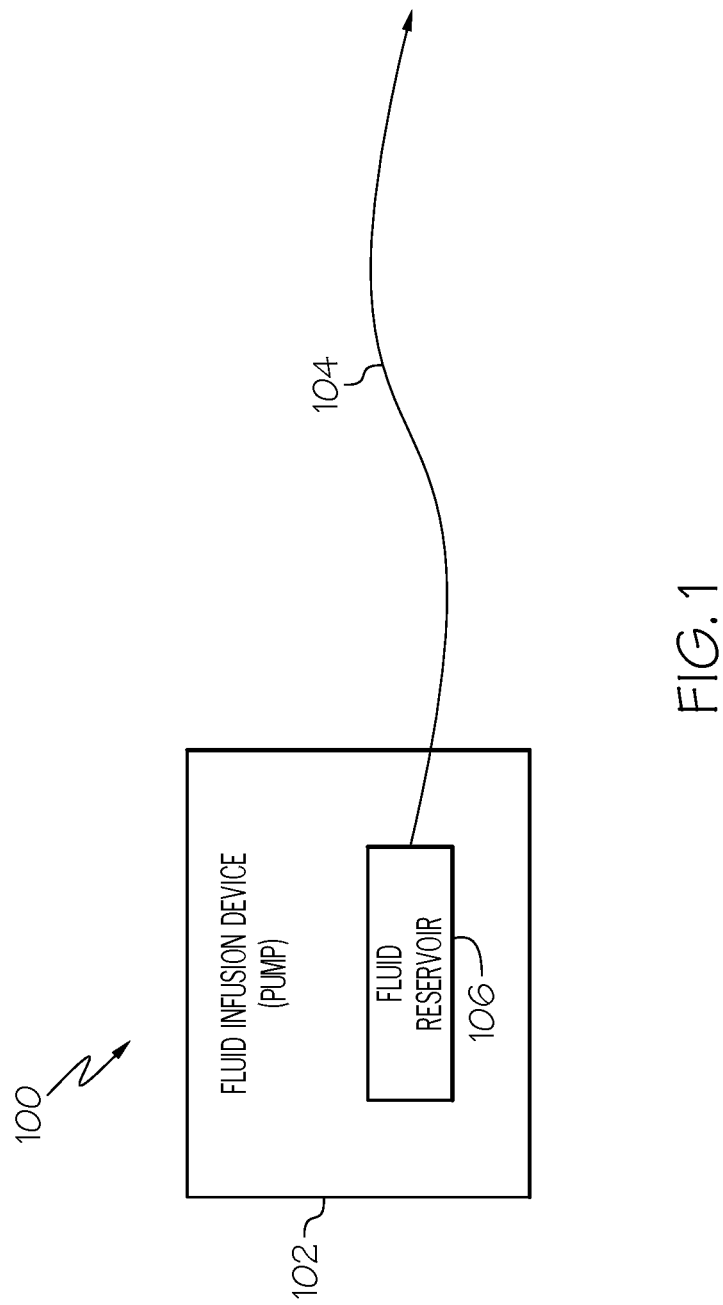
FIG. 1 is a simplified block diagram representation of an embodiment of a fluid delivery system according to various embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a simplified block diagram representation of an embodiment of a fluid delivery system 100, which can be utilized to administer a medication fluid such as insulin to a patient. The fluid delivery system 100 includes a fluid infusion device 102 (e.g., an infusion pump) and a fluid conduit assembly 104 that is coupled to, integrated with, or otherwise associated with the fluid infusion device 102. The fluid infusion device 102 includes a fluid reservoir 106 or an equivalent supply of the medication fluid to be administered. The fluid infusion device 102 is operated in a controlled manner to deliver the medication fluid to the user via the fluid conduit assembly 104. Although not depicted in FIG. 1, the fluid infusion device 102 also includes a set connector system for venting gas from the fluid reservoir 106.

Figure 2:
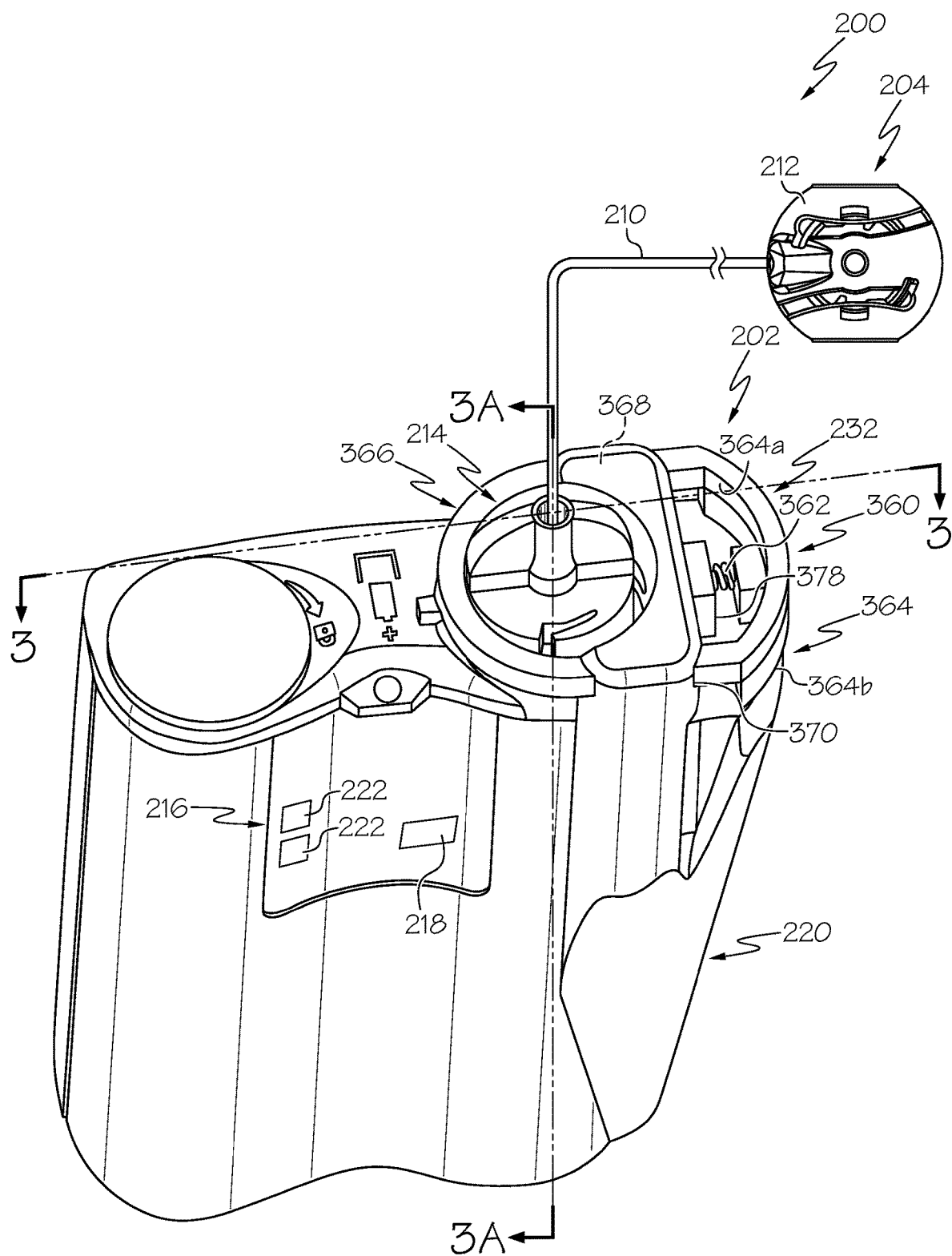
FIG. 2 is a plan view of an exemplary embodiment of a fluid delivery system that includes a fluid infusion device having an exemplary set connector system for venting a gas from a fluid reservoir according to the various teachings of the present disclosure.

The fluid infusion device 102 may be provided in any desired configuration or platform. In accordance with one non-limiting embodiment, the fluid infusion device is realized as a portable unit that can be carried or worn by the patient. In this regard, FIG. 2 is a plan view of an exemplary embodiment of a fluid delivery system 200 that includes a portable fluid infusion device 202 and a fluid conduit assembly that takes the form of an infusion set component 204. The infusion set component 204 is coupled to the fluid infusion device 202. The fluid infusion device 202 accommodates a fluid reservoir (shown in FIG. 3) for the medication fluid to be delivered to the user.

The illustrated embodiment of the infusion set component 204 includes, without limitation: a tube 210; an infusion unit 212 coupled to the distal end of the tube 210; and a set connector system 214 coupled to the proximal end of the tube 210. The infusion set component 204 defines a fluid flow path that fluidly couples the fluid reservoir to the infusion unit 212. The fluid infusion device 202 is designed to be carried or worn by the patient, and the infusion set component 204 terminates at the infusion unit 212 such that the fluid infusion device 202 can deliver fluid to the body of the patient via the tube 210. The fluid infusion device 202 may leverage a number of conventional features, components, elements, and characteristics of existing fluid infusion devices. For example, the fluid infusion device 202 may incorporate some of the features, components, elements, and/or characteristics described in U.S. Pat. Nos. 6,485,465 and 7,621,893, the relevant content of which is incorporated by reference herein.

In this example, the fluid infusion device 202 includes a user interface 216 and a display 218 coupled to a housing 220. The user interface 216 includes one or more input devices 222, which can be activated by the user. The user interface 216 can be used to administer a bolus of insulin, to change therapy settings, to change user preferences, to select display features, and the like. Although not required, the illustrated embodiment of the fluid infusion device 202 includes the display 218. The display 218 can be used to present various types of information or data to the user, such as, without limitation: the current glucose level of the patient; the time; a graph or chart of the patient's glucose level versus time; device status indicators, etc. In some embodiments, the display 218 is realized as a touch screen display element and, therefore, the display 218 also serves as a user interface component.

Figure 3:
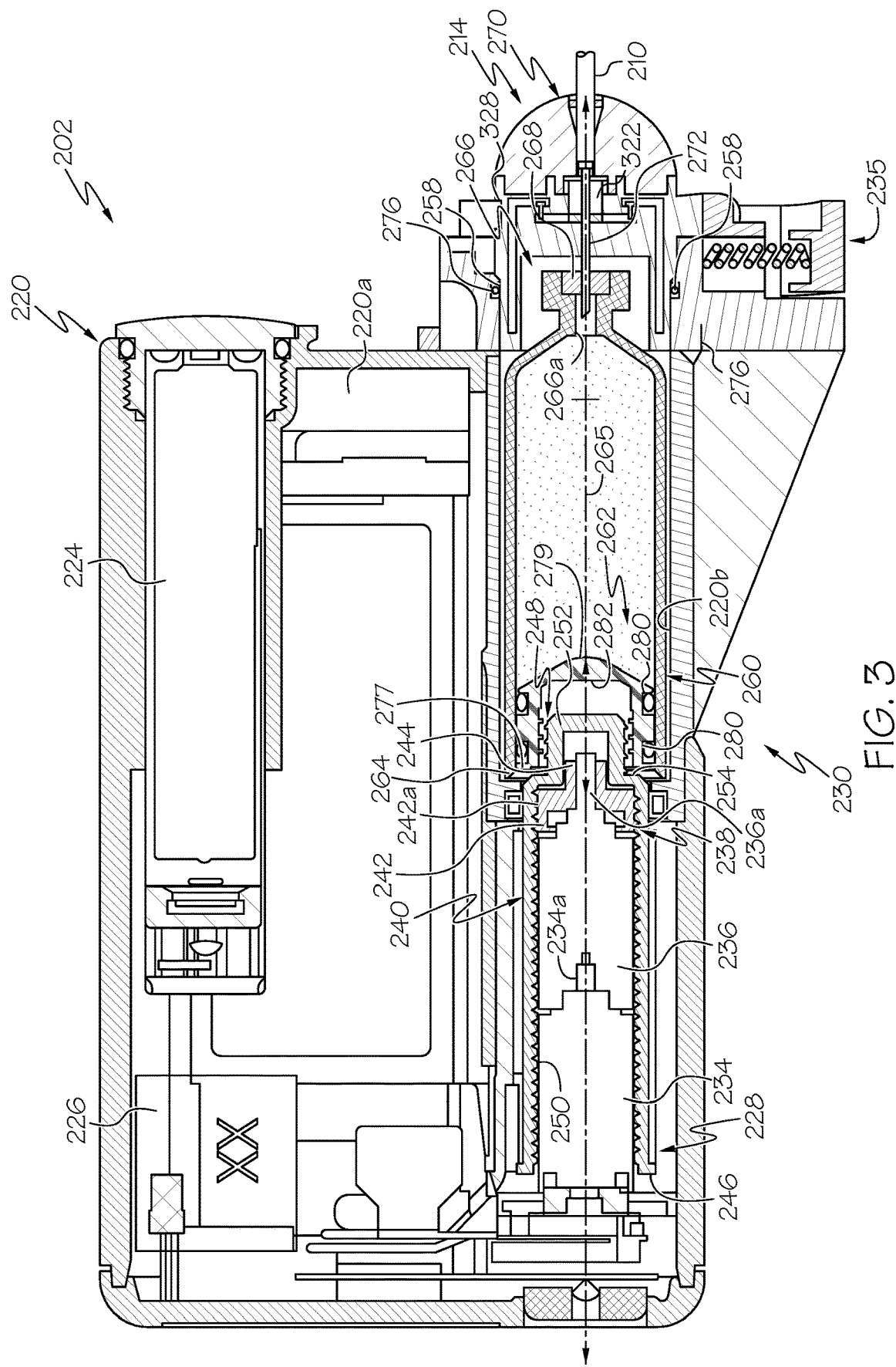
FIG. 3 is a cross-sectional view of the fluid infusion device of FIG. 2, taken along line 3-3 of FIG. 2.
Figure 3A:
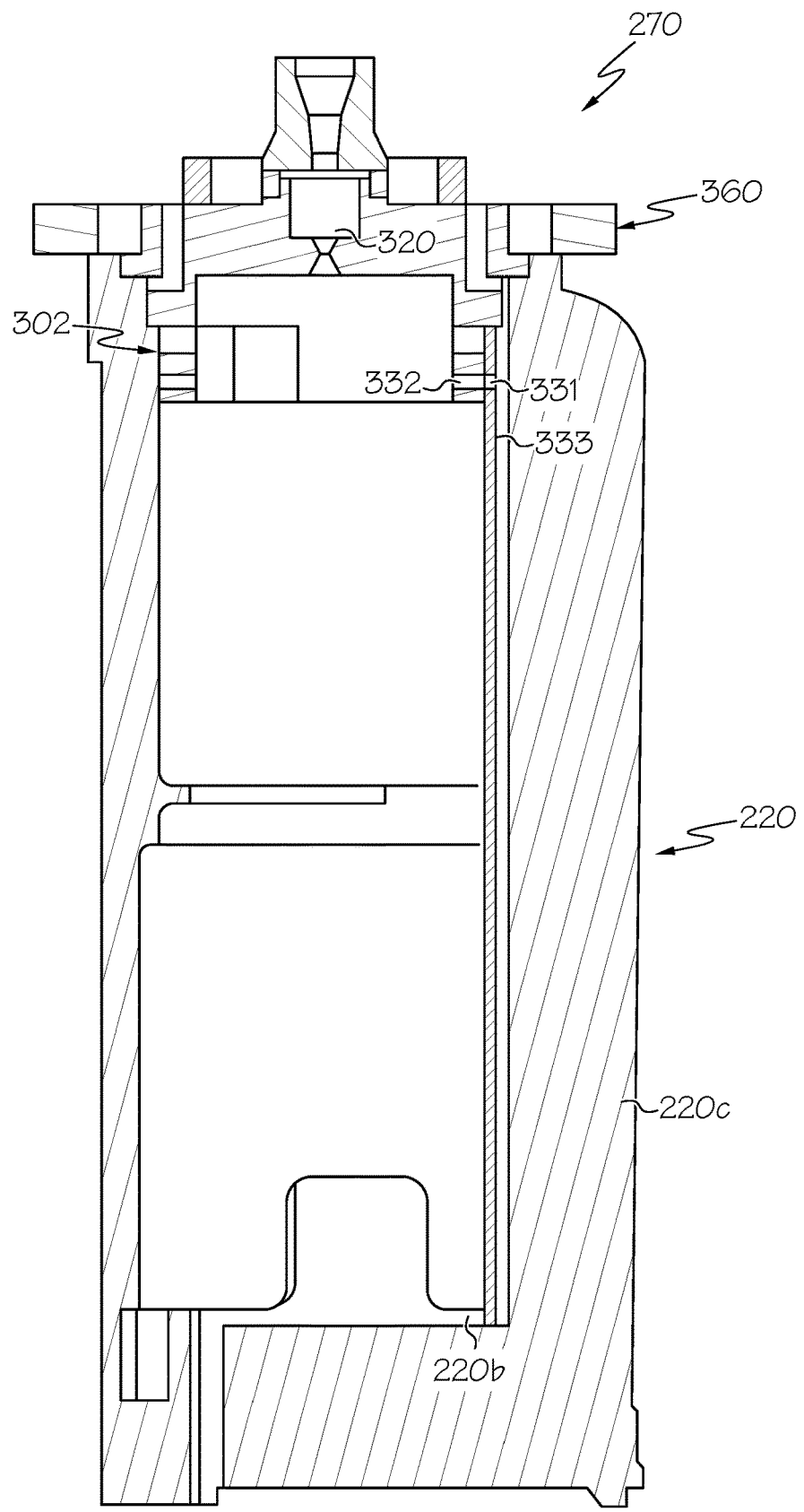
FIG. 3A is a cross-sectional view of the fluid infusion device of FIG. 2, taken along line 3A-3A of FIG. 2.

With reference to FIG. 3, the housing 220 of the fluid infusion device 202 accommodates a power supply 224, a controller or control module 226, a drive system 228 and a fluid reservoir system 230. In certain embodiments, the housing 220 also includes a lock 232, which securely couples the fluid reservoir system 230 to the housing 220 as will be discussed in greater detail herein. Generally, the power supply 224, the control module 226 and the drive system 228 are accommodated in a pump chamber 220*a* defined by the housing 220, and the fluid reservoir system 230 is accommodated in a reservoir chamber 220*b* defined by the housing 220. With reference to FIG. 3A, the housing 220 also includes a vent chamber 220*c*, which is defined adjacent to the reservoir chamber 220*b*. As will be discussed, the vent chamber 220*c* can be in fluid communication with the set connector system 214 to receive fluid, such as air, which is vented from the set connector system 214. The vent chamber 220*c* is generally fluidly separated from or not in fluid communication with the pump chamber 220*a*. The housing 220 can have any desired shape to accommodate the various components of the fluid infusion device 202, and thus, it will be understood that the shape and configuration of the housing 220 illustrated herein is merely exemplary.

With reference back to FIG. 3, the power supply 224 is any suitable device for supplying the fluid infusion device 202 with power, including, but not limited to, a battery. In one example, the power supply 224 can be removable relative to the housing 220; however, the power supply 224 can also be fixed within the housing 220. The control module 226 is in communication with the user interface 216, display 218, power supply 224 and drive system 228. The control module 226 controls the operation of the fluid infusion device 202 based on patient specific operating parameters. For example, the control module 226 controls the supply of power from the power supply 224 to the drive system 228 to activate the drive system 124 to dispense fluid from the fluid reservoir system 230. Further detail regarding the control of the fluid infusion device 202 can be found in U.S. Pat. Nos. 6,485,465 and 7,621,893, the relevant content of which was previously incorporated herein by reference.

The drive system 228 cooperates with the fluid reservoir system 230 to dispense the fluid from the fluid reservoir system 230. In one example, the drive system 228 includes a motor 234, a gear box 236, a drive screw 238 and a slide 240. The motor 234 receives power from the power supply 224 as controlled by the control module 226. In one example, the motor 234 is an electric motor. The motor 234 includes an output shaft 234*a*. The output shaft 234*a* is coupled to the gear box 236. In one embodiment, the gear box 236 is a reduction gear box. The gear box 236 includes an output shaft 236*a*, which is coupled to the drive screw 238.

The drive screw 238 includes a generally cylindrical distal portion 242 and a generally cylindrical proximal portion 244. The distal portion 242 has a diameter, which can be larger than a diameter of the proximal portion 244. The distal portion 242 includes a plurality of threads 242*a*. The plurality of threads 242*a* are generally formed about an exterior circumference of the distal portion 242. The proximal portion 244 is generally unthreaded, and can be sized to be received within a portion of the slide 240. The proximal portion 244 can serve to align the drive screw 238 within the slide 240 during assembly, for example.

With continued reference to FIG. 3, the slide 240 is substantially cylindrical and includes a distal slide end 246, a proximal slide end 248 and a plurality of threads 250. The distal slide end 246 is adjacent to the motor 234 when the slide 240 is in a first, fully retracted position and the proximal slide end 248 is adjacent to the drive screw 238 when the slide 240 is in the first, fully retracted position. The proximal slide end 248 includes a projection 252 and a shoulder 254, which cooperate with the fluid reservoir system 230 to dispense the fluid from the fluid reservoir system 230. The shoulder 254 is defined adjacent to the projection 252 and contacts a portion of the fluid reservoir system 230 to dispense fluid from the fluid reservoir system 230.

The plurality of threads 250 of the slide 240 are formed along an interior surface 240*a* of the slide 240 between the distal slide end 246 and the proximal slide end 248. The plurality of threads 250 are formed so as to threadably engage the threads 242*a* of the drive screw 238. Thus, the rotation of the drive screw 238 causes the linear translation of the slide 240.

In this regard, the slide 240 is generally sized such that in a first, retracted position, the motor 234, the gear box 236 and the drive screw 238 are substantially surrounded by the slide 240. The slide 240 is movable to a second, fully extended position through the operation of the motor 234. The slide 240 is also movable to a plurality of positions between the first, retracted position and the second, fully extended position via the operation of the motor 234. Generally, the operation of the motor 234 rotates the output shaft 234*a*, which is coupled to the gear box 236. The gear box 236 reduces the speed and increases the torque output by the motor 234, and the output shaft 236*a* of the gear box 236 rotates the drive screw 238, which moves along the threads 250 formed within the slide 240. The movement or rotation of the drive screw 238 relative to the slide 240 causes the movement or linear translation of the slide 240 within the housing 220. The forward advancement of the slide 240 (i.e. the movement of the slide 240 toward the fluid reservoir system 230) causes the fluid reservoir system 230 to dispense fluid.

With continued reference to FIG. 3, the fluid reservoir system 230 includes a fluid reservoir 256 and a sealing member 258. The fluid reservoir 256 and the sealing member 258 are each received within an opening defined by the housing 220. The sealing member 258 is coupled between the fluid reservoir 256 and the set connector system 214 to prevent the ingress of fluids into the reservoir chamber 220*b* of the housing 220. In one example, the sealing member 258 comprises an O-ring; however, any suitable device can be used to prevent the ingress of fluids, as known to one skilled in the art.

With reference to FIG. 3, the fluid reservoir 256 includes a body or barrel 260 and a stopper 262. The barrel 260 has a first or distal barrel end 264 and a second or proximal barrel end 266. Fluid 265 is retained within the barrel 260 between the distal barrel end 264 and the proximal barrel end 266. The distal barrel end 264 is positioned adjacent to the slide 240 when the fluid reservoir 256 is assembled in the housing 220. Generally, the distal barrel end 264 can have a substantially open perimeter or can be substantially circumferentially open such that the slide 240 is receivable within the barrel 260 through the distal barrel end 264.

The proximal barrel end 266 can have any desirable size and shape configured to mate with at least a portion of the set connector system 214, as will be discussed in further detail herein. In one example, the proximal barrel end 266 defines a passageway 266a through which the fluid 265 flows out of the fluid reservoir 256. The passageway 266a is closed by a septum 268. The septum 268 is received within a portion of the proximal barrel end 266, and is coupled to the proximal barrel end 266 through any suitable technique, such as ultrasonic welding, press-fit, etc. The septum 268 serves as a barrier to prevent the ingress of fluids into the fluid reservoir system 230, and prevents the egress of fluids from the fluid reservoir 256. The septum 268 is pierceable by the set connector system 214 to define a fluid flow path out of the fluid reservoir 256. In one example, the set connector system 214 includes a connector system 270, a hollow instrument or needle 272 and the tube 210. As will be discussed, the connector system 270 couples the needle 272 and the tube 210 to the fluid reservoir 256, and includes a vent subsystem 318 to vent trapped gas, such as air bubbles, which may be contained within the fluid reservoir 256, to the vent chamber 220c (FIG. 3A). The needle 272 defines a flow path for the fluid 265 out of the fluid reservoir 256, through the connector system 270 and into the tube 210.

In one example, the housing 220 includes a retaining system 276, which couples the set connector system 214 to the fluid reservoir 256. In one example, the retaining system 276 comprises one or more threads 276a and one or more notches (not shown). The one or more threads 276a threadably engage corresponding threads 278 (FIG. 4) defined in the connector system 270 to couple the connector system 270 to the fluid reservoir 256.

With reference to FIG. 3, the stopper 262 is disposed within the barrel 260. The stopper 262 is movable within and relative to the barrel 260 to dispense fluid from the fluid reservoir 256. When the barrel 260 is full of fluid, the stopper 262 is adjacent to the distal barrel end 264, and the stopper 262 is movable to a position adjacent to the proximal barrel end 266 to empty the fluid from the fluid reservoir 256. In one example, the stopper 262 is substantially cylindrical, and includes a distal stopper end 277, a proximal stopper end 279, at least one friction element 280 and a counterbore 282 defined from the distal stopper end 277 to the proximal stopper end 279.

The distal stopper end 277 is open about a perimeter of the distal stopper end 277, and thus, is generally circumferentially open. The proximal stopper end 279 is closed about a perimeter of the proximal stopper end 279, and thus, is generally circumferentially closed. The proximal stopper end 279 includes a slightly conical external surface; however, the proximal stopper end 279 can be flat, convex, etc. The at least one friction element 280 is coupled to the stopper 262 about an exterior surface of the stopper 262. In one example, the at least one friction element 280 comprises two friction elements, which include, but are not limited to, O-rings. The friction elements 280 are coupled to circumferential grooves defined in the exterior surface of the stopper 262.

The counterbore 282 receives the projection 252 of the slide 240 and the movement of the slide 240 causes the shoulder 254 of the slide 240 to contact and move the stopper 262. In one example, the counterbore 282 includes threads; however, the projection 252 of the slide 240 is not threadably engaged with the stopper 262. Thus, the threads illustrated herein are merely exemplary.

With reference to FIG. 3, the set connector system 214 mates with and couples to the proximal barrel end 266 of the fluid reservoir 256, establishing the fluid path from the fluid reservoir 256 to the tube 210. The set connector system 214 is coupled to the housing 220 of the fluid infusion device 202 and to the fluid reservoir 256 to seal and secure the fluid reservoir 256 inside the housing 220. Thereafter, actuation of the fluid infusion device 202 causes the medication fluid to be expelled from the fluid reservoir 256, through the infusion set component 204, and into the body of the patient via the infusion unit 212 at the distal end of the tube 210. Accordingly, when the set connector system 214 is installed as depicted in FIG. 3, the tube 210 extends from the fluid infusion device 202 to the infusion unit 212 and the needle 272 provides a fluid pathway to the body of the patient. For the illustrated embodiment, the set connector system 214 is realized as a removable reservoir cap (or fitting) that is suitably sized and configured to accommodate replacement of fluid reservoirs (which are typically disposable) as needed.

Figure 4:
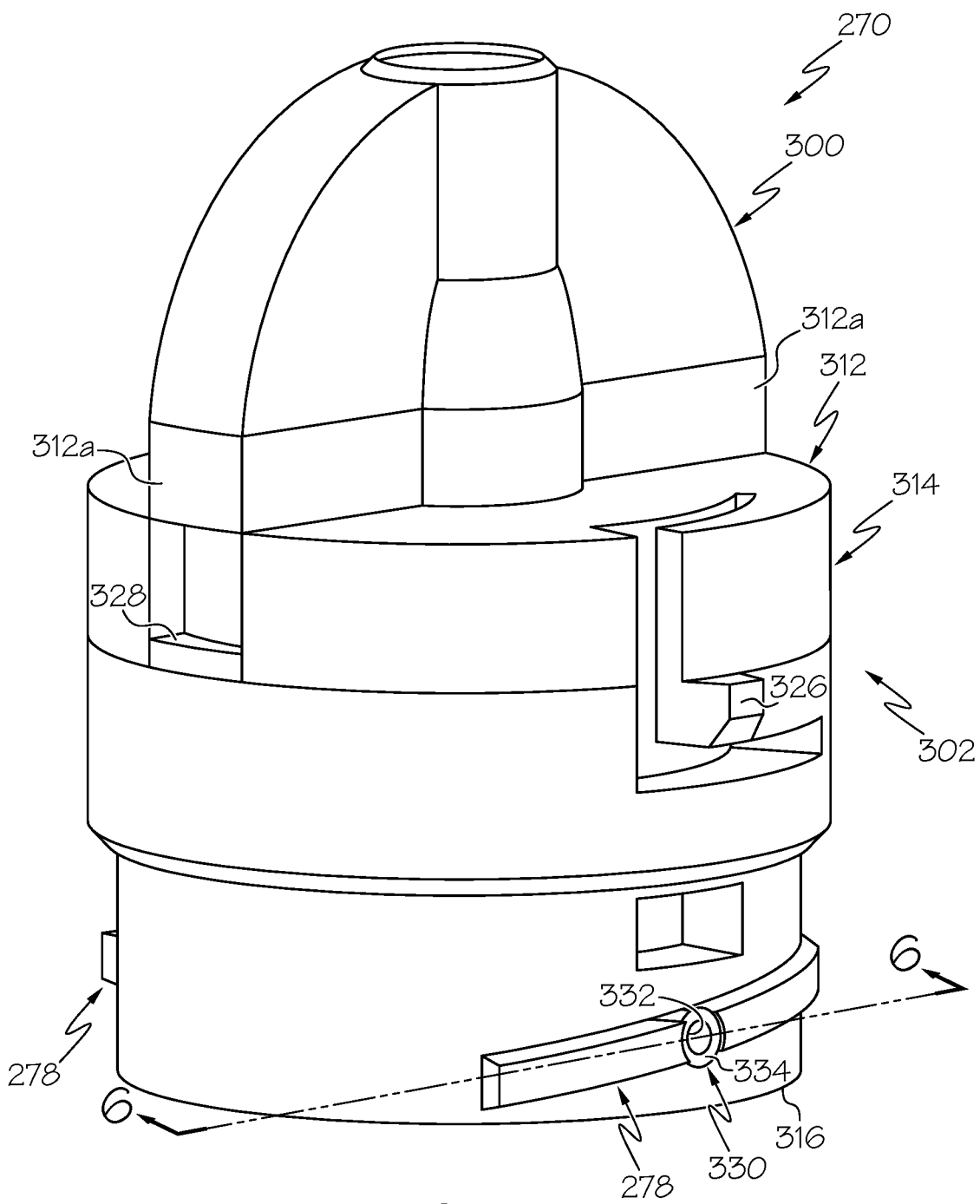
FIG. 4 is a perspective view of a connector system of the set connector system of FIG. 2 according to the various teachings of the present disclosure.

With reference to FIG. 4, the connector system 270 of the set connector system 214 is shown in greater detail. In FIG. 4, the connector system 270 is illustrated without the tube 210 for clarity. The connector system 270 is removably coupled to the housing 220 and retains the fluid reservoir 256 within the housing 220. In this example, the connector system 270 includes a first body section 300 and a second body section 302. Each of the first body section 300 and the second body section 302 are composed of a polymeric material, such as a polycarbonate material, and the first body section 300 and the second body section 302 can each be formed through any suitable technique, such as injection molding, or 3D printing, for example. It should be noted that although the first body section 300 and the second body section 302 are illustrated as being discrete components, the first body section 300 and the second body section 302 can be integrally formed or one-piece (monolithic), if desired.

Figure 5:
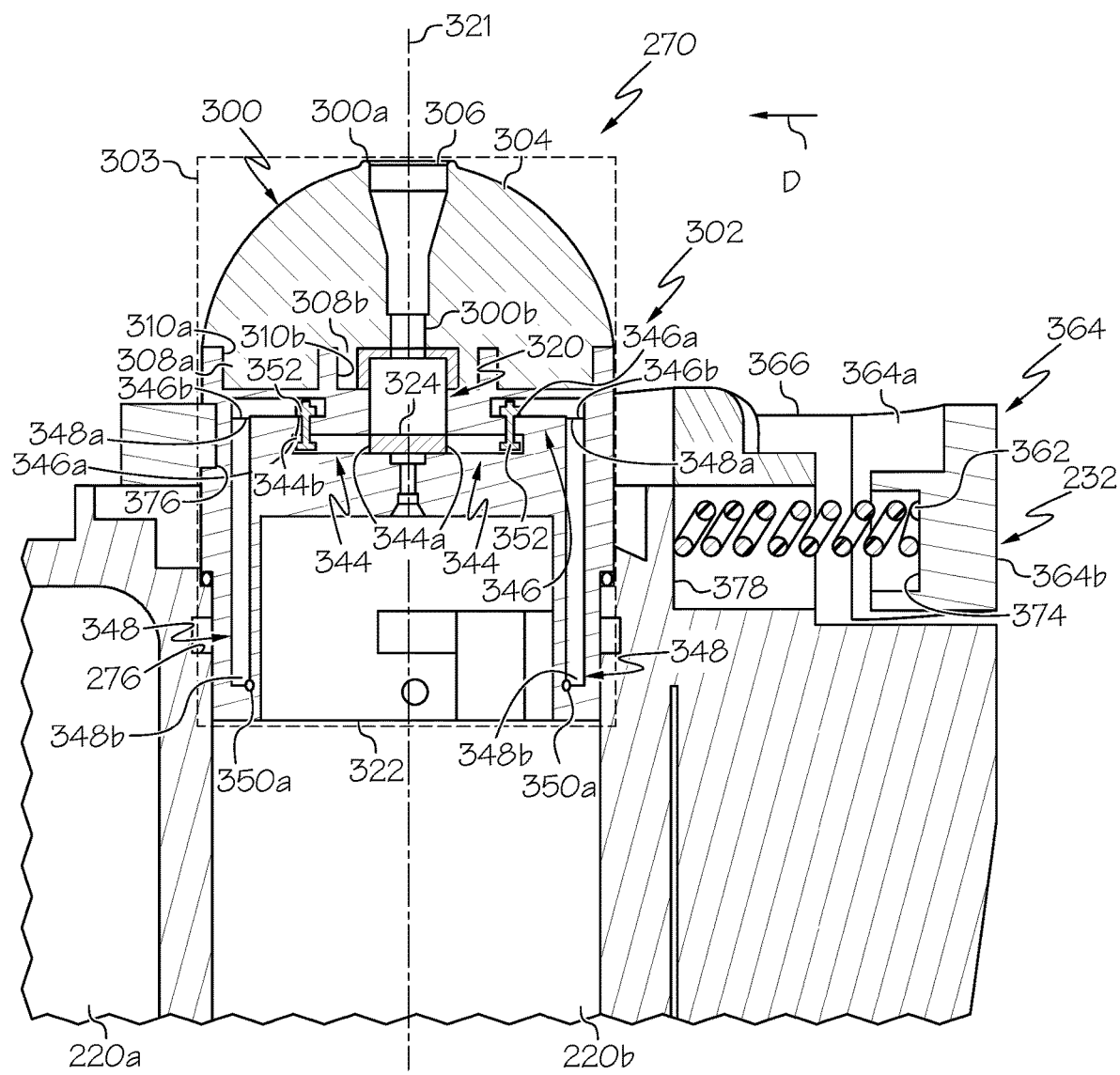
FIG. 5 is a detail cross-sectional view of the connector system of FIG. 4, taken from detail 5 of the cross-sectional view of FIG. 2.

The first body section 300 includes a graspable portion 304 and defines a bore 306. The graspable portion 304 enables the manipulation of the connector system 270 by a user, to remove or insert the connector system 270, and thus the fluid reservoir 256, from the housing 220. With reference to FIG. 5, FIG. 5 provides a detail view of the cross-section of FIG. 3, in which the fluid reservoir 256, the needle 272 and the tube 210 are removed for clarity. As shown in FIG. 5, the bore 306 extends from a first end 300a of the first body section 300 to a second end 300b of the first body section 300. The bore 306 receives the tube 210 and the needle 272, and generally, the tube 210 is coupled adjacent to the needle 272 within the bore 306 to define the fluid flow path out of the connector system 270. The second end 300b can also include one or more tabs 308. In this example, the second end 300b defines two tabs 308a having a first width and two tabs 308b having a second width. The first width is different than the second width, and generally, the second width is less than the first width. The tabs 308b can be defined adjacent to the bore 306, and the tabs 308a can be spaced radially outward from the bore 306. The tabs 308a, 308b are each spaced apart from each other on the second end 300b. The two tabs 308a, 308b are received in corresponding channels 310a, 310b of the second body section 302. The tabs 308a, 308b can be fixedly coupled to the channels 310a, 310b, via ultrasonic welding, adhesives, etc.

The second body section 302 is received within the housing 220, to retain the fluid reservoir 256 (FIG. 3) within the housing 220. The second body section 302 has a plane of symmetry 303. With reference back to FIG. 4, the second body section 302 is generally annular, and includes a first end 312, a sidewall 314, a second end 316 and a vent subsystem 318. The first end 312 defines the channels 310a, 310b, and also includes an annular chamber 320. The channels 310a, 310b and the annular chamber 320 may be defined by common walls 312a, which extend outwardly from a surface of the first end 312. With reference to FIG. 5, the annular chamber 320 extends from the first end 312 to a counterbore 322 of the second end 316. The annular chamber 320 is coaxial with the bore 306, and is coaxial with the counterbore 322 to receive the needle 272 therethrough to define the fluid flow path from the fluid reservoir 256 to the tube 210 (FIG. 3). Generally, the bore 306, the annular chamber 320 and the counterbore 322 extend along an axis that defines a longitudinal axis 321 of the connector system 270.

In various embodiments, the annular chamber 320 also receives a filter 324. In one example, the needle 272 terminates adjacent to the filter 324, such that the needle 272 and the tube 210 are on opposite sides of the filter 324 to ensure that the fluid exiting the fluid reservoir 256 flows through the filter 324 (FIG. 3). In one example, a minimum volume of the annular chamber 320 is about 0.7 microliters (mL). Generally, the annular chamber 320 has a height that enables the needle 272 to be received within the annular chamber 320 without piercing the filter 324. The annular chamber 320 can be sterilized prior to the insertion of the filter 324, and further, the annular chamber 320 can be plasma treated to increase hydrophilicity, if desired.

The filter 324 comprises a gas trapping filter, and is formed from a suitable material, composition, or element such that the medication fluid can easily pass through the filter 324 during fluid delivery operations. The filter 324 can be formed from a hydrophilic, semi-hydrophilic, partially hydrophilic, or predominantly hydrophilic material. Although a truly hydrophilic material may be ideal, the material used for the filter 324 can be partially or predominantly hydrophilic while exhibiting some amount of hydrophobicity. In practice, the filter 324 can exhibit up to fifty percent hydrophobicity without adversely impacting the desired performance. For example, the filter 324 may include or be fabricated from a hydrophilic membrane, a hydrophilic sponge material, or a hydrophilic foam material. As explained below, the filter 324 also serves to filter particulates from the medication fluid during fluid delivery operations. Accordingly, the filter 324 has a pore size that is small enough to inhibit the flow of particulates. In certain embodiments, the pore size is within the range of about 0.45 to 5.00 microns, which is suitable for most medical applications. Non-limiting examples of suitable materials for the filter 324 include: polyacrylate; polyurethane; nylon; cellulose acetate; polyvinyl alcohol; polyethelene foam; polyvinyl acetate; polyester fiber felt; polyester (PET); polysulfone; polyethyl sulfone; collagen; polycaprolactone; or the like. It should be appreciated that the material or materials used to fabricate the filter 324 can be treated to enhance the hydrophilic characteristics if so desired.

One function of the filter 324 is to inhibit the downstream flow of air bubbles. Depending on the particular composition and configuration of the filter 324, air bubbles can be blocked by the filter 324 and/or retained within the filter 324 as the liquid medication flows downstream. Thus, the filter 324 may be realized as a gas impermeable membrane or material that also exhibits good hydrophilic properties. Accordingly, no air bubbles are present in the medication fluid that resides downstream from the filter 324.

Another benefit of the filter 324 relates to the volume accuracy of the fluid delivery system. In certain implementations, syringe pumps are calibrated to deliver a specified volume in response to a controlled mechanical actuation (e.g., movement of the syringe plunger in response to controlled rotation of an electric motor). Reducing or eliminating air from the fluid delivery path increases the accuracy of the volume calibrations.

In certain embodiments, the filter 324 also serves to filter particulates from the medication fluid such that the particulate count of the downstream medication fluid is reduced. As mentioned above, the material used to fabricate the filter 324 can be selected with a desired pore size to accommodate filtering of particulates having an expected size.

In some embodiments, the filter 324 also serves to absorb and/or adsorb certain substances, chemicals, or suspended elements from the medication fluid. For example, the filter 324 may include material that is configured or treated to absorb/adsorb lubricating or manufacturing oil that is associated with the manufacturing, assembly, or maintenance of one or more components of the fluid reservoir system 230. In this regard, a fluid reservoir for insulin can be fabricated with a trace amount of silicone oil that serves as a lubricant for the plunger of the fluid reservoir 256. Accordingly, the filter 324 can include a material, layer, or treatment that reduces, traps, or otherwise removes some or all of the silicone oil from the medication fluid as it passes through the filter 324.

In certain embodiments, the filter 324 also serves as a drug depot during operation of the fluid delivery system. To this end, the filter 324 can include a drug, medicine, chemical, or composition impregnated therein (or coated thereon, or otherwise carried by the filter 324). A quantity of the drug is released into the medication fluid as the fluid flows through the filter 324 during a fluid delivery operation. The drug carried by the filter 324 can be selected to address the needs of the particular patient, fluid delivery system, medication fluid, etc. In accordance with the exemplary insulin infusion system described here, the filter 324 is impregnated with a drug that treats the patient site to extend the useful life of the fluid infusion set. For example, the filter 324 can be treated with an anticoagulant such as Heparin or Dextran. As another example, the filter 324 can be impregnated or infused with an anti-proliferative drug such as Rapamycin. It should be appreciated that these examples are neither exhaustive nor restrictive, and that the filter 324 can be impregnated, treated, or infused with any drug that may be appropriate and suitable for the particular medical condition, fluid delivery system, or application. Generally, the gas trapped by the filter 324 (e.g. air bubbles) is vented from the connector system 270 to the vent chamber 220c (FIG. 3A) by the vent subsystem 318, as will be discussed further herein.

With reference back to FIG. 4, the sidewall 314 extends about the perimeter or circumference of the second body section 302. The sidewall 314 includes a pair of arms 326, the threads 278 and a lock receptacle 328. The arms 326 are substantially opposite each other about the sidewall 314. The arms 326 are generally integrally formed with the sidewall 314, and include a living hinge that biases the arms 326 in a direction away from the sidewall 314. Stated another way, each of the arms 326 are defined so as to be biased radially outward from the second body section 302. The engagement of the second body section 302 with the housing 220 causes the compression of the arms 326, until the arms 326 expand and engage a respective pocket (not shown) defined in the reservoir chamber 220b of the housing 220. Thus, in this example, the arms 326 cooperate with the lock 232 to secure the second body section 302 to the housing 220. Generally, the arms 326 also provide tactile feedback that the connector system 270 is threaded fully into the housing 220.

The threads 278 are defined about a portion of the sidewall 314, so as to be adjacent to the second end 316. In this example, the threads 278 comprise two threads; however, any number of threads can be employed to couple the connector system 270 to the housing 220. In this example, each of the threads 278 defines an outlet 330. The outlet 330 is in fluid communication with the vent subsystem 318 and is in fluid communication with the vent chamber 220c to vent the gas (e.g. air bubbles) trapped by the filter 324 to the vent chamber 220c (FIG. 3A). In one example, with reference to FIG. 3A, each outlet 330 is in fluid communication with a respective bore 331 defined through a wall 333 that separates the vent chamber 220c from the reservoir chamber 220b. With reference back to FIG. 3, the outlet 330 includes a bore 332 and a seal 334. The bore 332 is generally defined near a mid-point of the respective thread 278; however the bore 332 can be defined through the respective thread 278 at any desired location. The bore 332 is generally circular; however, the bore 332 can have any desired shape. The seal 334 generally circumscribes the bore 332, and thus, the seal 334 is generally annular. In one example, the seal 334 comprises an O-ring; however, the seal 334 can comprise any suitable sealing device. The seal 334 creates a seal between the second body section 302 and the wall 333 dividing the vent chamber 220c and the reservoir chamber 220b to prevent the flow of fluids into the vent chamber 220c.

The lock receptacle 328 receives a portion of the lock 232 to secure or lock the connector system 270 to the housing 220. In one example, the lock receptacle 328 is substantially rectangular; however, the lock receptacle 328 can have any desired shape that cooperates with the lock 232 to secure or lock the connector system 270 to the housing 220.

With reference to FIG. 5, the second end 316 defines the counterbore 322. In certain embodiments, a second membrane can be disposed adjacent to or coupled to the second end 316 to enable air to vent from the reservoir chamber 220b, while preventing fluid from exiting the reservoir chamber 220b. In one example, the second membrane comprises a fluoropolymeric membrane. Generally, the second membrane has a defined breakthrough pressure, which allows only gas, such as air, to pass through the second membrane, and not liquids.

The vent subsystem 318 is in fluid communication with the annular chamber 320 to transfer the gas captured by the filter 324 from the annular chamber 320 to the vent chamber 220c of the housing 220. The vent subsystem 318 includes a first conduit 340 and a second conduit 342, which each terminate at a respective outlet 330. Generally, the first conduit 340 is defined on a first side of the second body section 302, and the second conduit 342 is defined on an opposite side of the second body section 302, such that the trapped gas is directed from the annular chamber 320 in at least two different directions to enter the vent chamber 220c via a respective one of the outlets 330. Although the vent subsystem 318 is described and illustrated herein as comprising two conduits, the first conduit 340 and the second conduit 342, it will be understood that the vent subsystem 318 can include any number of conduits.

Each of the first conduit 340 and the second conduit 342 include a first conduit passage 344, a second conduit passage 346, a third conduit passage 348 and a fourth conduit passage 350. Each of the first conduit passage 344, the second conduit passage 346, the third conduit passage 348 and the fourth conduit passage 350 are in fluid communication to enable the transfer of gas, such as the trapped air, from the annular chamber 320 to the respective outlet 330.

The first conduit passage 344 has a first inlet 344a in fluid communication with the annular chamber 320, such that the filter 324 is adjacent to the first inlet 344a. The first conduit passage 344 has a first outlet 344b, which is downstream from the first inlet 344a. The first conduit passage 344 extends radially outward from the annular chamber 320, and extends along an axis that is substantially transverse, and in one example, substantially perpendicular to the longitudinal axis 321.

In this example, a first valve 352 is coupled between the first outlet 344b, and a second inlet 346a of the second conduit passage 346. The first valve 352 comprises a suitable one-way valve, including, but not limited to, a poppet valve, a duckbill valve, an umbrella valve, and so on. The first valve 352 permits the flow of the trapped gas from the first outlet 344b to the second inlet 346a in a single direction only, thereby preventing or inhibiting a back flow into the first conduit passage 344.

The second conduit passage 346 also includes a second outlet 346b, which is downstream from the second inlet 346a. The second outlet 346b is in fluid communication with a third inlet 348a of the third conduit passage 348. The second conduit passage 346 extends radially outward from the annular chamber 320, and extends along an axis that is substantially transverse, and in one example, substantially perpendicular to the longitudinal axis 321. In this example, the second conduit passage 346 is spaced apart from the first conduit passage 344, and is fluidly coupled to the first conduit passage 344 via the first valve 352.

The third conduit passage 348 includes a third outlet 348b, which is in fluid communication with a fourth inlet 350a of the fourth conduit passage 350. The third conduit passage 348 extends substantially along an axis that is substantially parallel to the longitudinal axis 321.

Figure 6:
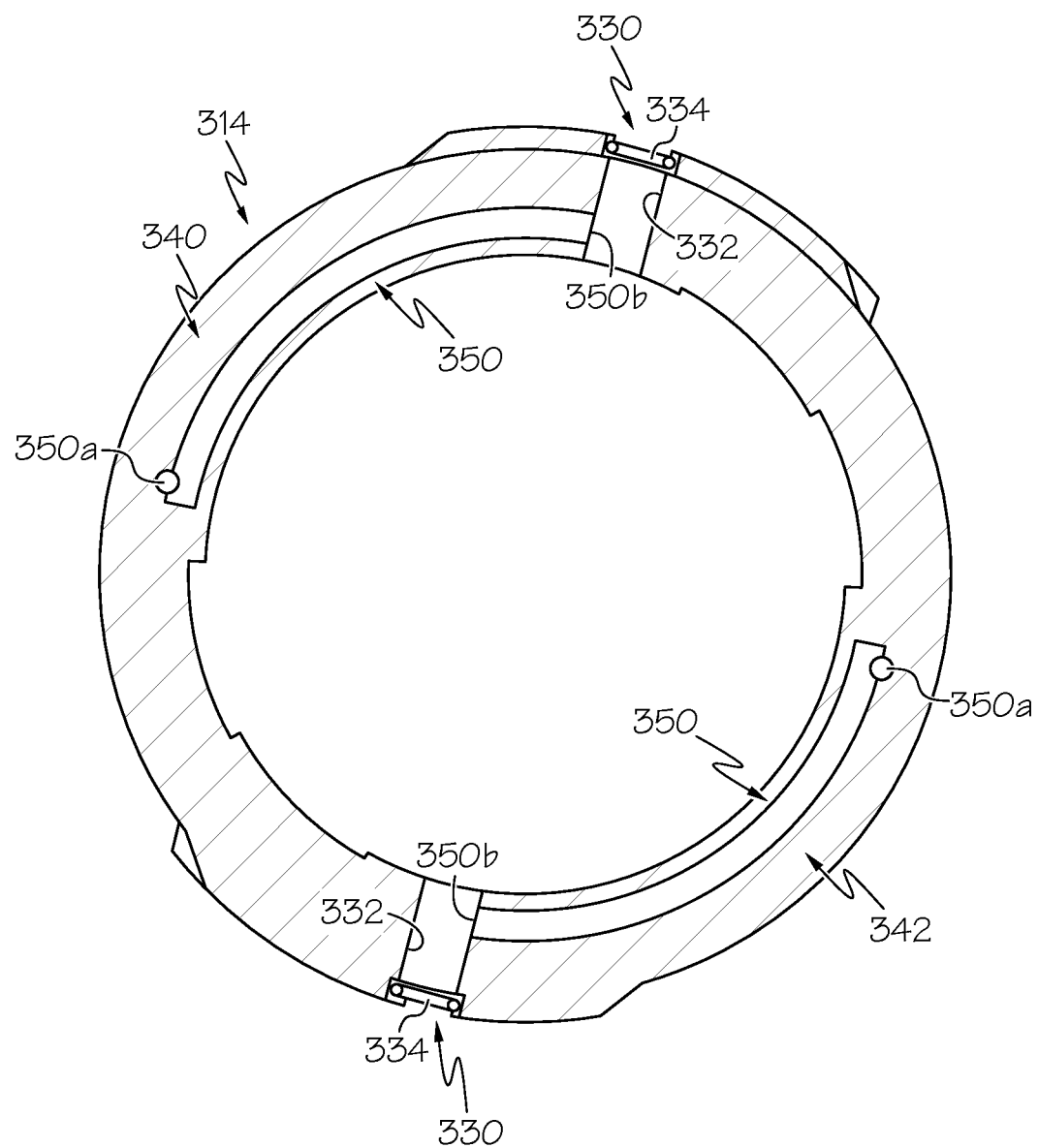
FIG. 6 is a cross-sectional view of the connector system of FIG. 4, taken along line 6-6 of FIG. 4.

With reference to FIG. 6, the fourth conduit passage 350 is shown in greater detail. The fourth conduit passage 350 extends along an arc defined by the sidewall 314. The fourth conduit passage 350 includes a fourth outlet 350b, which is in fluid communication with the bore 332 of the respective outlet 330.

With reference back to FIG. 2, the lock 232 securely couples the connector system 270 to the housing 220. In one example, the lock 232 includes a locking member 360 and a biasing member or spring 362. The locking member 360 is substantially D-shaped, and includes a base 364 and a curved lock arm 366. The locking member 360 is slidably received within a first guide 368 and a second guide 370 defined through a portion of the housing 220. In this example, a respective portion of the curved lock arm 366 is slidably received within a respective one of the first guide 368 and the second guide 370; however, it will be understood that other configurations are possible.

The base 364 is curved, and generally follows a curvature of the housing 220, although it will be understood that the base 364 can be flat or planar. With reference to FIG. 5, the base 364 defines an interior surface 364a, which is opposite an exterior surface 364b. The interior surface 364a is coupled to the curved lock arm 366 and defines a first spring seat 374. The first spring seat 374 receives an end of the spring 362. With reference back to FIG. 2, the exterior surface 364b provides a contact surface for a user to touch to disengage the lock 232, and thereby release the connector system 270, and the fluid reservoir 256, from the housing 220.

The curved lock arm 366 extends about a perimeter or circumference of the second body section 302 of the connector system 270. In this example, with reference to FIG.

5, the curved lock arm 366 includes a tab 376, which is configured to engage the lock receptacle 328 of the second body section 302 to secure the connector system 270 to the housing 220.

The spring 362 biases the locking member 360 in a first, locked position, as shown in FIG. 5. The spring 362 has a first end, which biases against the first spring seat 374, and a second end, which biases against a second spring seat 378 defined by a portion of the housing 220. Generally, the spring 362 comprises a coil spring composed of a metal or metal alloy, but the spring 362 can comprise any suitable biasing member. The base 364 of the locking member 360 is movable in a direction D from the first, locked position to a second, release position, to compress the spring 362 and thereby release the connector system 270 from the housing 220.

With reference to FIG. 3, with the housing 220 assembled with the power supply 224, the control module 226 and the drive system 228, the fluid reservoir system 230 can be coupled to the housing 220. In one example, a full fluid reservoir 256 is inserted into the housing 220 such that the stopper 262 is adjacent to the projection 252 of the slide 240. The set connector system 214, with the needle 272 and the tube 210 coupled to the connector system 270, is then coupled to the housing 220. In one example, with reference to FIG. 5, the base 364 is moved in the direction D, to define an opening for receipt of the connector system 270. The connector system 270 is inserted into the housing 220 and rotated, by the first body section 300, for example, such that the threads 278 engage the threads 276a of the housing 220. The connector system 270 is rotated until the arms 326 engage corresponding pockets defined in the reservoir chamber 220b to couple the connector system 270 to the housing 220. The base 364 of the lock 232 is released, and the spring 362 causes the tab 376 to engage the lock receptacle 328, thereby fixedly coupling or securing the set connector system 214 to the housing 220.

With the set connector system 214 fixedly coupled or secured to the housing 220, the needle 272 pierces the septum 268, thereby defining a fluid flow path for the fluid 265 out of the fluid reservoir 256. With the set connector system 214 coupled to the fluid reservoir 256, one or more control signals from the control module 226 can drive the motor 234, thereby rotating the drive screw 238, which results in the linear translation of the slide 240. The advancement of the slide 240 into the fluid reservoir 256 moves the stopper 262, causing the fluid 265 to flow from the fluid reservoir 256 through the fluid flow path defined by the set connector system 214.

As the fluid flows through the needle 272, the fluid passes through the filter 324. Any gas (e.g. air bubbles) within the fluid is trapped by the filter 324. As the reservoir chamber 220b is generally operating under a pressure, which is greater than a pressure in the vent chamber 220c, the trapped gas is drawn through the filter 324 into the first conduit 340 and the second conduit 342. The gas trapped by the filter 324 flows from the filter 324 into the first inlet 344a of the first conduit passage 344 of each of the first conduit 340 and the second conduit 342. The pressure of the gas in the first conduit passage 344 causes the first valve 352 to open, thereby exhausting the gas from the first conduit passage 344 into the second conduit passage 346. From the second conduit passage 346, the gas flows to the third conduit passage 348 and from the third conduit passage 348 the gas flows into the fourth conduit passage 350. The gas flows from the fourth conduit passage 350 and exits into the bore 332 of the respective outlet 330, before being exhausted into the vent chamber 220c (FIG. 3A).

In order to remove the set connector system 214, for example, to replace an empty fluid reservoir 256, with reference to FIG. 5, a force can be applied in the direction D to the base 364 to bias the lock 232 into the second, release position. With the lock 232 in the second, release position, the first body section 300 can be rotated to overcome the force of the arms 326, and to uncouple the second body section 302 from the threads 276a. The connector system 270 can then be removed from the housing 220, and the force can be removed from the base 364. With the force removed from the base 364, the spring 362 returns the lock 232 to the first, locked position.

Figure 7:
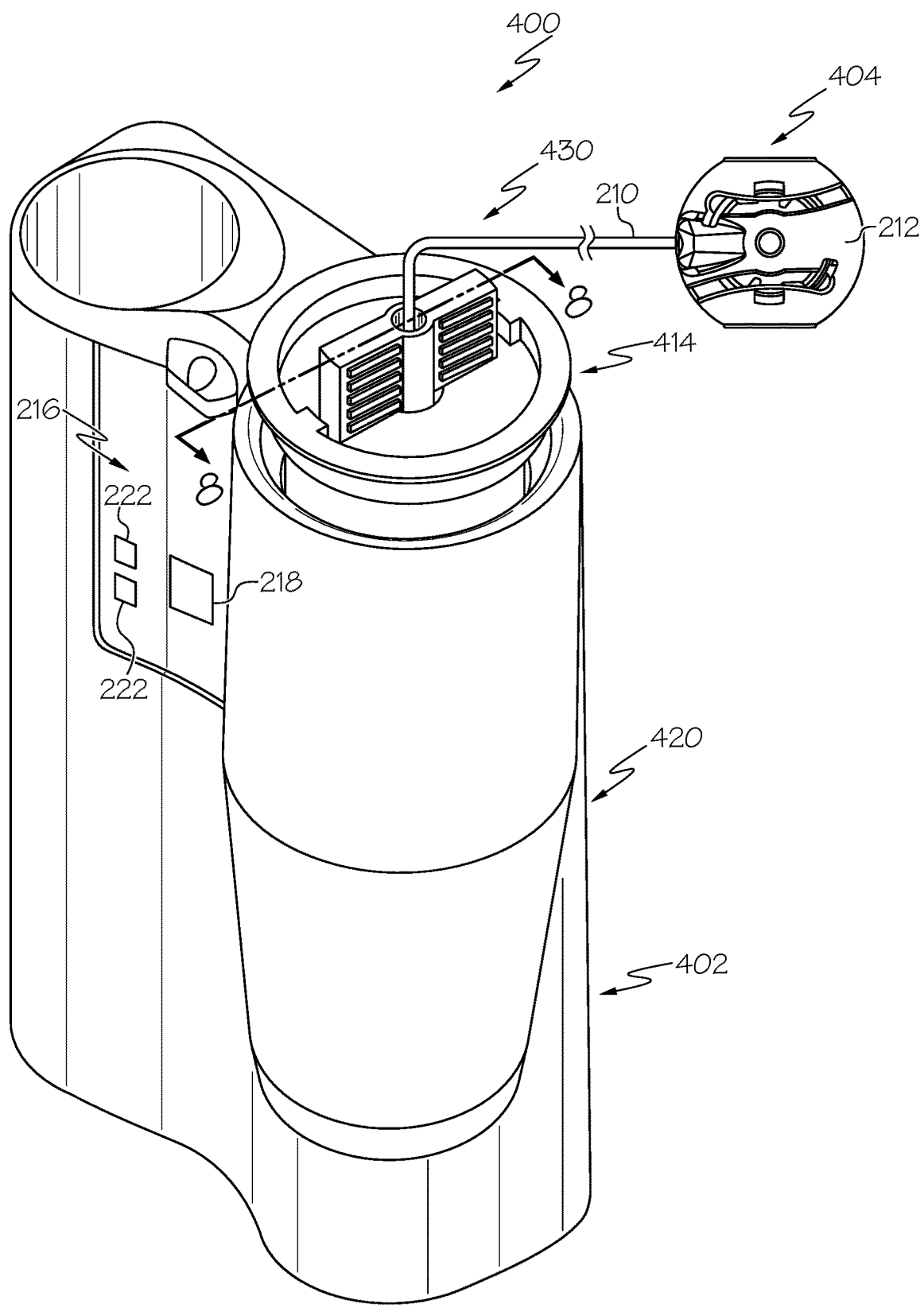
FIG. 7 is a plan view of an exemplary embodiment of a fluid delivery system that includes a fluid infusion device having an exemplary set connector system for venting a gas from a fluid reservoir according to the various teachings of the present disclosure.

With reference to FIG. 7, a plan view of an exemplary embodiment of a fluid delivery system 400 that includes a portable fluid infusion device 402 and a fluid conduit assembly that takes the form of an infusion set component 404. The infusion set component 404 is coupled to the fluid infusion device 402. The fluid infusion device 402 accommodates a fluid reservoir, such as the fluid reservoir 256 (FIG. 3), for the medication fluid to be delivered to the user. As the fluid infusion device 402 and the infusion set component 404 are substantially similar to the fluid infusion device 202 and the infusion set component 204 discussed with regard to FIGS. 1-6, only the differences in the fluid infusion device 402 and the fluid infusion device 202; and the infusion set component 404 and the infusion set component 204 will be discussed in great detail herein.

The infusion set component 404 includes, without limitation: the tube 210; the infusion unit 212 coupled to the distal end of the tube 210; and a set connector system 414 coupled to the proximal end of the tube 210. The infusion set component 404 defines a fluid flow path that fluidly couples the fluid reservoir to the infusion unit 212. The fluid infusion device 402 is designed to be carried or worn by the patient, and the infusion set component 404 terminates at the infusion unit 212 such that the fluid infusion device 402 can deliver fluid to the body of the patient via the tube 210. The fluid infusion device 402 may leverage a number of conventional features, components, elements, and characteristics of existing fluid infusion devices. For example, the fluid infusion device 402 may incorporate some of the features, components, elements, and/or characteristics described in U.S. Pat. Nos. 6,485,465 and 7,621,893, the relevant content of which is incorporated by reference herein.

The fluid infusion device 402 includes the user interface 216 and the display 218 coupled to a housing 420. The user interface 216 includes the one or more input devices 222, which can be activated by the user. The housing 420 of the fluid infusion device 202 accommodates the power supply 224 (FIG. 3), the controller or control module 226 (FIG. 3), the drive system 228 (FIG. 3) and a fluid reservoir system 430. Generally, the power supply 224, the control module 226 and the drive system 228 are accommodated in the pump chamber 220a (FIG. 3) defined by the housing 420, and the fluid reservoir system 430 is accommodated in the reservoir chamber 220b (FIG. 8) defined by the housing 420. The housing 420 can have any desired shape to accommodate the various components of the fluid infusion device 402, and thus, it will be understood that the shape and configuration of the housing 420 illustrated herein is merely exemplary.

Figure 8:
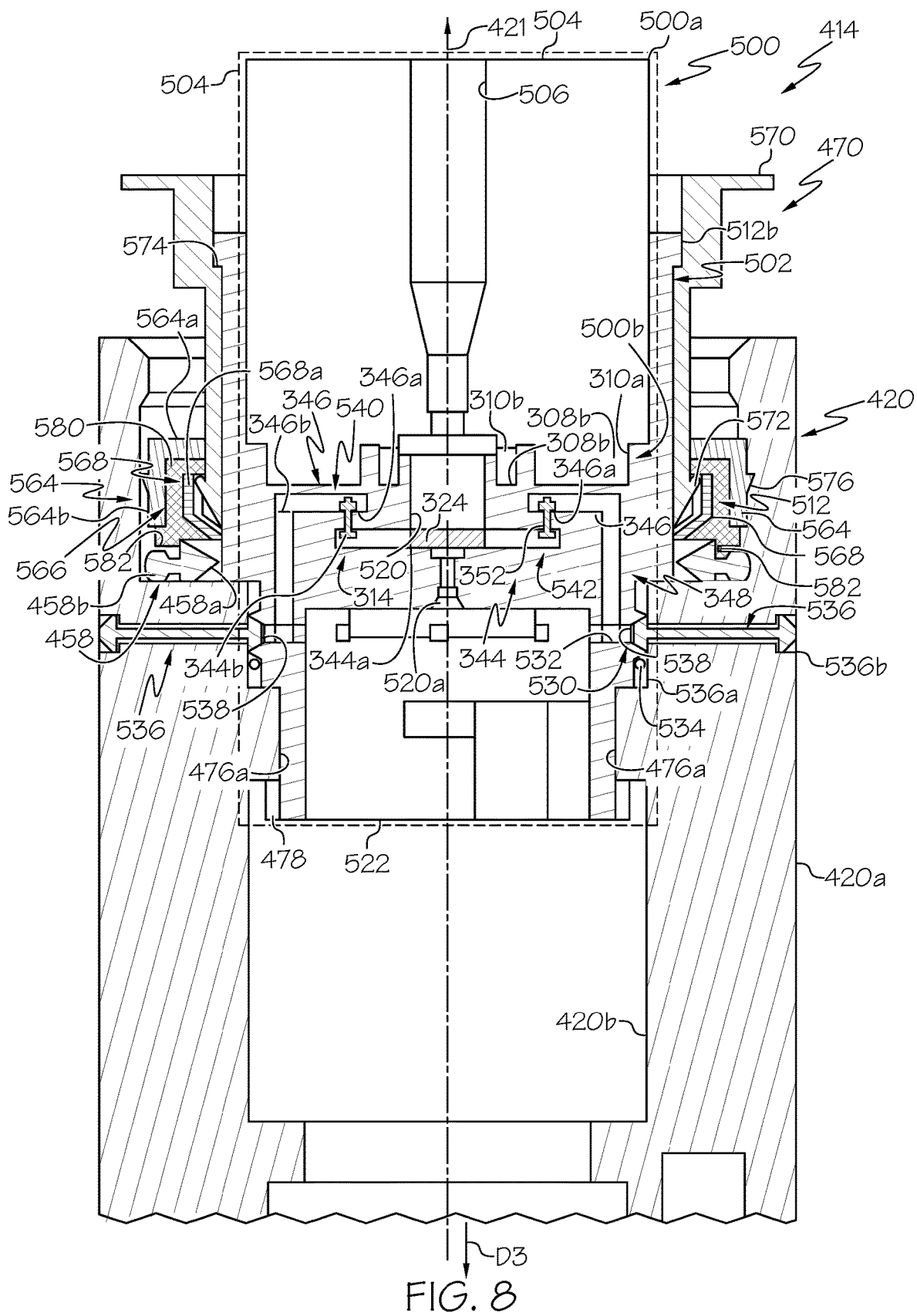
FIG. 8 is a is a cross-sectional view of the fluid infusion device of FIG. 7, taken along line 8-8 of FIG. 7.

With reference to FIG. 8, the fluid reservoir system 430 includes the fluid reservoir 256 (FIG. 3) and a sealing member 458. The fluid reservoir 256 and the sealing member 458 are each received within an opening defined by the housing 420. The sealing member 458 is coupled about a perimeter of a portion of the set connector system 414 to prevent the ingress of fluids into the reservoir chamber 420b of the housing 420. In one example, the sealing member 458 comprises an O-ring; however, any suitable device can be used to prevent the ingress of fluids, as known to one skilled in the art. In this example, the sealing member 458 includes a triangular end 458a and a notched trailing end 458b. The triangular end 458a contacts a connector system 470 of the set connector system 414. The notched trailing end 458b can contact one or more rings 560 associated with the housing 420, as will be discussed in further detail below.

The set connector system 414 includes a connector system 470, the needle 272 and the tube 210. As will be discussed, the connector system 470 couples the needle 272 and the tube 210 to the fluid reservoir 256 (FIG. 3), and includes a vent subsystem 518 to vent trapped gas, for example, air bubbles, which may be contained within the fluid reservoir 256, to an ambient environment surrounding the housing 420. The needle 272 defines a flow path for the fluid 265 out of the fluid reservoir 256, through the connector system 470 and into the tube 210.

In one example, the housing 420 includes a retaining system 476, which couples the set connector system 414 to the fluid reservoir 256 (FIG. 3). In one example, the retaining system 476 comprises one or more rails 476a. The one or more rails 476a are defined on opposing walls of the reservoir chamber 220b, and generally extend along an axis that is substantially parallel with a longitudinal axis 421 of the housing 420, and cooperate to receive corresponding grooves 478 defined in the connector system 470 to assist in retaining the connector system 470 within the housing 420. In this example, the reservoir chamber 220b includes two rails 476a and the connector system 470 includes two grooves 478, which are spaced apart about a perimeter or circumference of the connector system 470, however, the reservoir chamber 220b and the connector system 470 can have any number of rails 476a and grooves 478, respectively. Generally, each groove 478 is defined about the connector system 470 so as to be substantially opposite the other groove 478.

With reference to FIG. 7, the set connector system 414 mates with and couples to the proximal barrel end 266 of the fluid reservoir 256 (FIG. 3), establishing the fluid path from the fluid reservoir 256 to the tube 210. The set connector system 414 is coupled to the housing 420 of the fluid infusion device 202 and to the fluid reservoir 256 (FIG. 3) to seal and secure the fluid reservoir 256 inside the housing 420. Thereafter, actuation of the fluid infusion device 402 causes the medication fluid to be expelled from the fluid reservoir 256, through the infusion set component 204, and into the body of the patient via the infusion unit 212 at the distal end of the tube 210. Accordingly, when the set connector system 414 is installed as depicted in FIG. 7, the tube 210 extends from the fluid infusion device 202 to the infusion unit 212 and the needle 272 provides a fluid pathway to the body of the patient. For the illustrated embodiment, the set connector system 414 is realized as a removable reservoir cap (or fitting) that is suitably sized and configured to accommodate replacement of fluid reservoirs (which are typically disposable) as needed.

With reference to FIG. 8, the connector system 470 of the set connector system 414 is shown in greater detail. In FIG. 8, the connector system 470 is illustrated without the needle 272 and the tube 210 for clarity. The connector system 470 is removably coupled to the housing 420 and retains the fluid reservoir 256 within the housing 420. In this example, the connector system 470 includes a first body section 500 and a second body section 502. Each of the first body section 500 and the second body section 502 are composed of a polymeric material, such as a polycarbonate material, and the first body section 500 and the second body section 502 can each be formed through any suitable technique, such as injection molding, or 3D printing, for example. It should be noted that although the first body section 500 and the second body section 502 are illustrated as being discrete components, the first body section 500 and the second body section 502 can be integrally formed or one-piece (monolithic), if desired.

The first body section 500 includes a graspable portion 504 and defines a bore 506. The graspable portion 504 enables the manipulation of the connector system 470 by a user, to remove or insert the connector system 470, and thus the fluid reservoir 256, from the housing 420. The bore 506 extends from a first end 500a of the first body section 500 to a second end 500b of the first body section 500. The bore 506 receives the tube 210 and the needle 272, and generally, the tube 210 is coupled adjacent to the needle 272 within the bore 506 to define the fluid flow path out of the connector system 470. The second end 500b can also include the one or more tabs 308. In this example, the second end 500b defines the two tabs 308a having the first width and the two tabs 308b having the second width. The two tabs 308a, 308b are received in corresponding channels 310a, 310b of the second body section 502. The tabs 308a, 308b can be fixedly coupled to the channels 310a, 310b, via ultrasonic welding, adhesives, etc.

Figure 9:
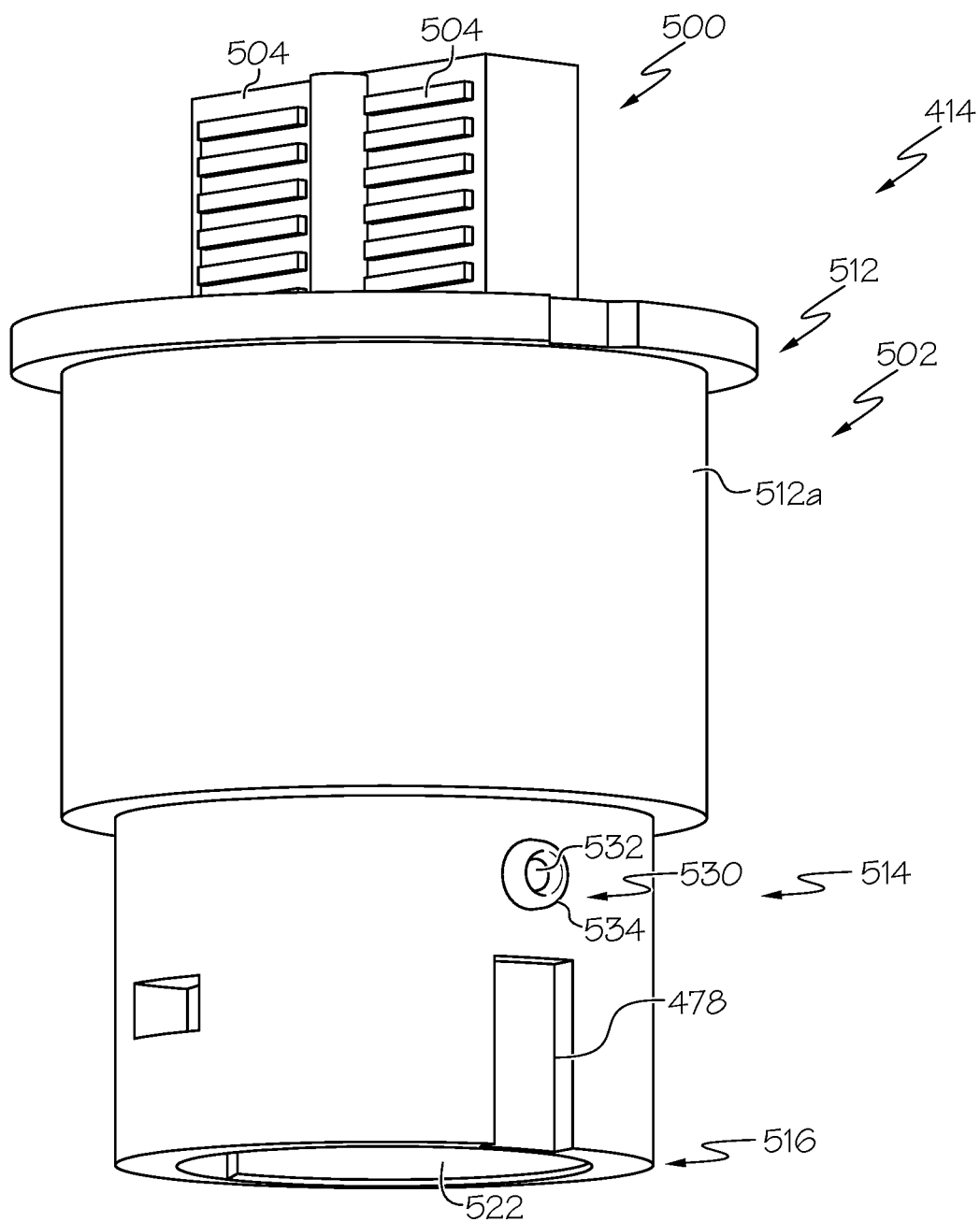
FIG. 9 is a perspective view of a connector system of the set connector system of FIG. 7 according to the various teachings of the present disclosure.

The second body section 502 is received within the housing 420, to retain the fluid reservoir 256 (FIG. 3) within the housing 420. The second body section 502 has a plane of symmetry 503. With reference to FIG. 9, the second body section 502 is generally annular, and includes a first end 512, a sidewall 514, a second end 516 and a vent subsystem 518 (FIG. 8). The first end 512 defines the channels 310a, 310b, and also includes an annular chamber 520 (FIG. 8). The channels 310a, 310b and the annular chamber 520 may be surrounded by a flange 512a, which extends upwardly about the perimeter of the second body section 502 from a surface of the first end 512 to provide additional strength to the first body section 500.

With reference to FIG. 8, the annular chamber 520 extends from the first end 512 to an area adjacent to a counterbore 522 of the second end 516. In one example, the annular chamber 520 is coupled to the counterbore 522 via a passageway 520a, which is sized to receive the needle 272 (FIG. 3). The annular chamber 520 is coaxial with the bore 506, and is coaxial with the passageway 520a and the counterbore 522 to receive the needle 272 therethrough to define the fluid flow path from the fluid reservoir 256 to the tube 210. Generally, the bore 506, the annular chamber 520, the passageway 520a and the counterbore 522 extend along an axis that is substantially parallel with the longitudinal axis 421.

In various embodiments, the annular chamber 520 also receives the filter 324. In this example, the needle 272 terminates adjacent to the filter 324, such that the needle 272 and the tube 210 are on opposite sides of the filter 324 to ensure that the fluid exiting the fluid reservoir 256 flows through the filter 324 (FIG. 3). In one example, a minimum volume of the annular chamber 520 is about 0.7 microliters (mL). Generally, the annular chamber 520 has a height that enables the needle 272 to be received within the annular chamber 520 without piercing the filter 324. The annular chamber 520 can be sterilized prior to the insertion of the filter 324, and further, the annular chamber 520 can be plasma treated to increase hydrophilicity, if desired. Generally, the gas (e.g. air bubbles) trapped by the filter 324 is vented from the connector system 470 to the ambient environment external to the housing 220 by the vent subsystem 518, as will be discussed further herein.

With reference back to FIG. 9, the sidewall 514 extends about the perimeter or circumference of the second body section 502, and cooperates with the flange 512a to define an exterior surface of the second body section 502. The sidewall 514 includes the grooves 478 and one or more outlets 530. In this example, the outlets 530 comprise two outlets 530, which are spaced apart from a respective one of the grooves 478. The grooves 478 are defined through the sidewall 514 from the second end 516 in a direction towards the first end 512.

Each outlet 530 is in fluid communication with the vent subsystem 518 and is in fluid communication with a respective conduit 536 defined through the housing 420 (FIG. 8) to vent the air trapped by the filter 324 to an ambient environment surrounding the housing 420. Each outlet 530 includes a bore 532 and a seal 534. The bore 532 is generally circular; however, the bore 532 can have any desired shape. The seal 534 generally circumscribes the bore 532, and thus, the seal 534 is generally annular. In one example, the seal 534 comprises an O-ring; however, the seal 534 can comprise any suitable sealing device. The seal 534 creates a seal between the second body section 302 and the reservoir chamber 420b to ensure that the trapped gas passes into the conduit 536 (FIG. 8).

With reference to FIG. 8, a membrane 538 substantially surrounds the outlets 530 and the conduit 536. The membrane 538 is positioned between each of the outlets 530 and each of the conduits 536 to assist in removing gas trapped in the reservoir chamber 220b. In one example, the membrane 538 comprises a fluoropolymeric membrane. Generally, the membrane 538 has a defined breakthrough pressure, which allows only gas, such as air, to pass through the membrane 538, and not liquids. The second end 516 defines the counterbore 522.

The vent subsystem 518 is in fluid communication with the annular chamber 520 to transfer the gas captured by the filter 324 from the annular chamber 520 to the conduits 536 of the housing 420. The vent subsystem 518 includes a first conduit 540 and a second conduit 542, which each terminate at a respective outlet 530. Generally, the first conduit 540 is defined on a first side of the second body section 502, and the second conduit 542 is defined on an opposite side of the second body section 502, such that the trapped gas is directed from the annular chamber 520 in at least two different directions to enter the conduits 536 via a respective one of the outlets 530. Although the vent subsystem 518 is described and illustrated herein as comprising two conduits, the first conduit 540 and the second conduit 542, it will be understood that the vent subsystem 518 can include any number of conduits.

Each of the first conduit 540 and the second conduit 542 include the first conduit passage 344, the second conduit passage 346 and the third conduit passage 348. Each of the first conduit passage 344, the second conduit passage 346 and the third conduit passage 348 are in fluid communication to enable the transfer of gas, such as the trapped air, from the annular chamber 520 to the respective outlet 530. In this example, the first valve 352 is coupled between the first outlet 344b, and the second inlet 346a of the second conduit passage 346. The third conduit passage 348 includes the third outlet 348b, which is in fluid communication with the bore 532 of the respective outlet 530.

The conduits 536 are defined on substantially opposite sides of the housing 420, and extend from the reservoir chamber 420b to an exterior surface 420a of the housing 420. The conduits 536 include a conduit inlet 536a, which is fluidly coupled to the respective outlet 530 to receive the trapped gas from the filter 324. The conduits 536 also include a conduit outlet 536b, which is defined at the exterior surface 420a of the housing 420. In one example, a second valve 550 is received substantially entirely through each of the conduits 536. The second valve 550 comprises a suitable one-way valve, including, but not limited to, a poppet valve, a duckbill valve, an umbrella valve, and so on. The second valve 550 permits the flow of the trapped gas from the conduit inlet 536a to the conduit outlet 536b and into the ambient environment in a single direction only, thereby preventing or inhibiting a back flow of fluids, including liquids and gasses, into the reservoir chamber 420b.

Figure 10:
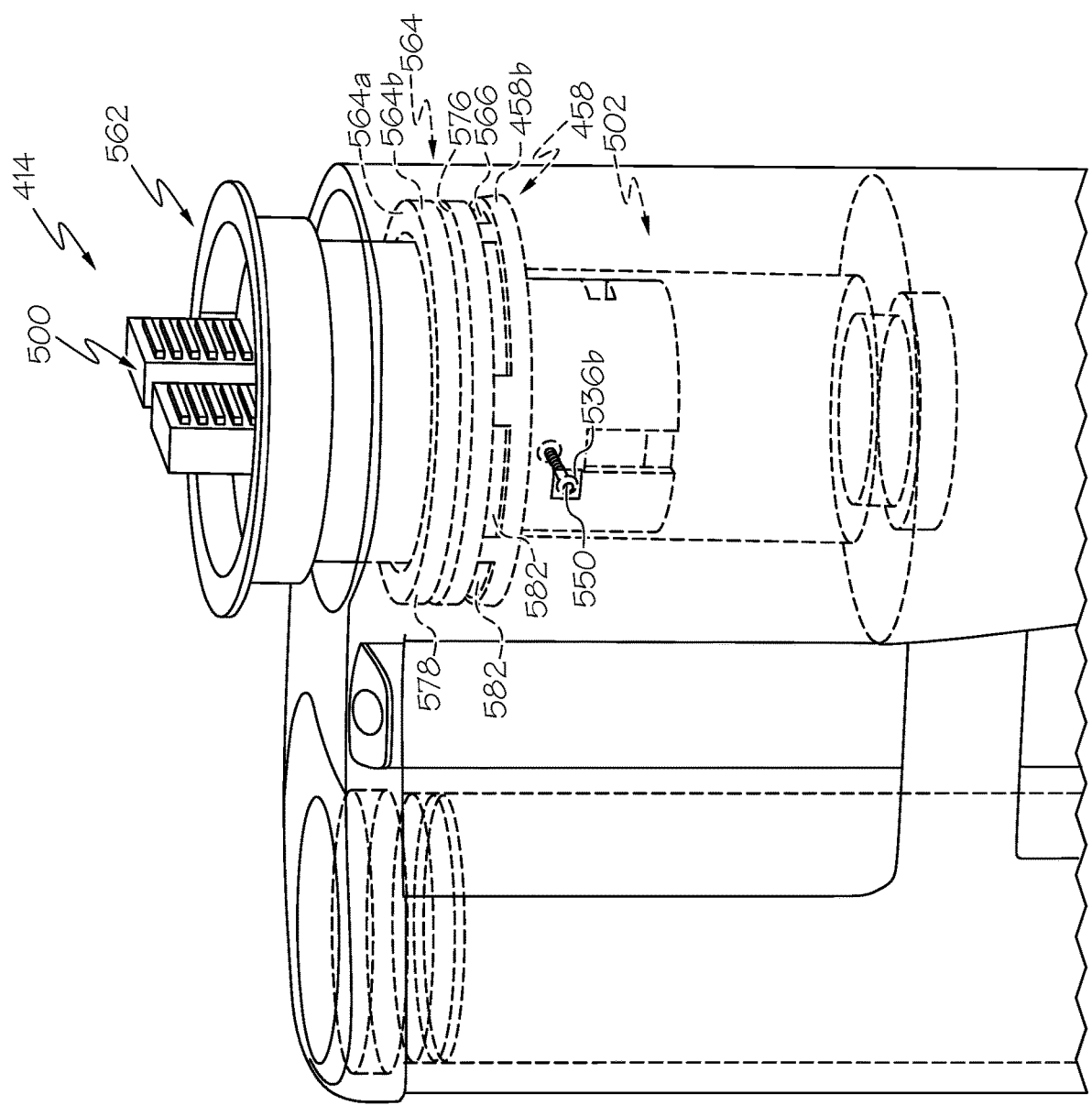
FIG. 10 is a perspective view of the fluid infusion device or FIG. 7, in which a portion of a housing of the fluid infusion device is illustrated in phantom.

With reference to FIG. 10, the housing 420 also includes one or more rings 560 that cooperate to securely couple the connector system 470 to the reservoir chamber 420b, and thus, the housing 420. In FIG. 10, the tube 210 and the infusion unit 212 are removed for clarity, and a portion of the housing 420 is illustrated in phantom. In this example, with reference to FIG. 10A, the one or more rings 560 comprise a release ring 562, a compliance ring 564, a retainer ring 566 and an anchoring ring 568 (FIG. 8).

The release ring 562 extends about a circumference of the first body section 500. With reference to FIG. 8, the release ring 562 includes a collar 570 and a tab 572 defined about an exterior surface of the release ring 562. The collar 570 provides a grasping surface for a user to manipulate the release ring 562, and the tab 572 cooperates with the retainer ring 566 to couple or decouple the connector system 470 from the housing 420. The release ring 562 also includes a ledge 574 defined about an inner surface of the release ring 562. The ledge 574 cooperates with a lip 512b of the flange 512a to couple the first body section 500 to the release ring 562. The release ring 562 can be composed of any suitable material, and in one example, the release ring 562 is composed of a polycarbonate polymeric material. It should be noted, however, that the release ring 562 can be composed of any suitable material, such as a polymer, metal or ceramic material. The release ring 562 can be molded as one piece, or can be printed, via 3D printing, for example.

The compliance ring 564 surrounds the first body section 500 when the connector system 470 is coupled to the housing 420. The compliance ring 564 is substantially L-shaped in cross-section. The compliance ring 564 can be composed of any suitable material, and in one example, the compliance ring 564 is composed of a polymeric material. In one example, the compliance ring 564 is composed of a polymeric, rubber-like material, such as a polyurethane thermoplastic material. The compliance ring 564 can be molded as one piece, or can be printed, via 3D printing, for example. With reference to FIG. 10, the compliance ring 564 includes a first leg 564a, which is substantially perpendicular to a second leg 564b. The second leg 564b of the compliance ring 564 can include a projection 576. The projection 576 cooperates with a notch 578 of the housing 420 to couple or secure the compliance ring 564 to the housing 420.

Figure 10A:
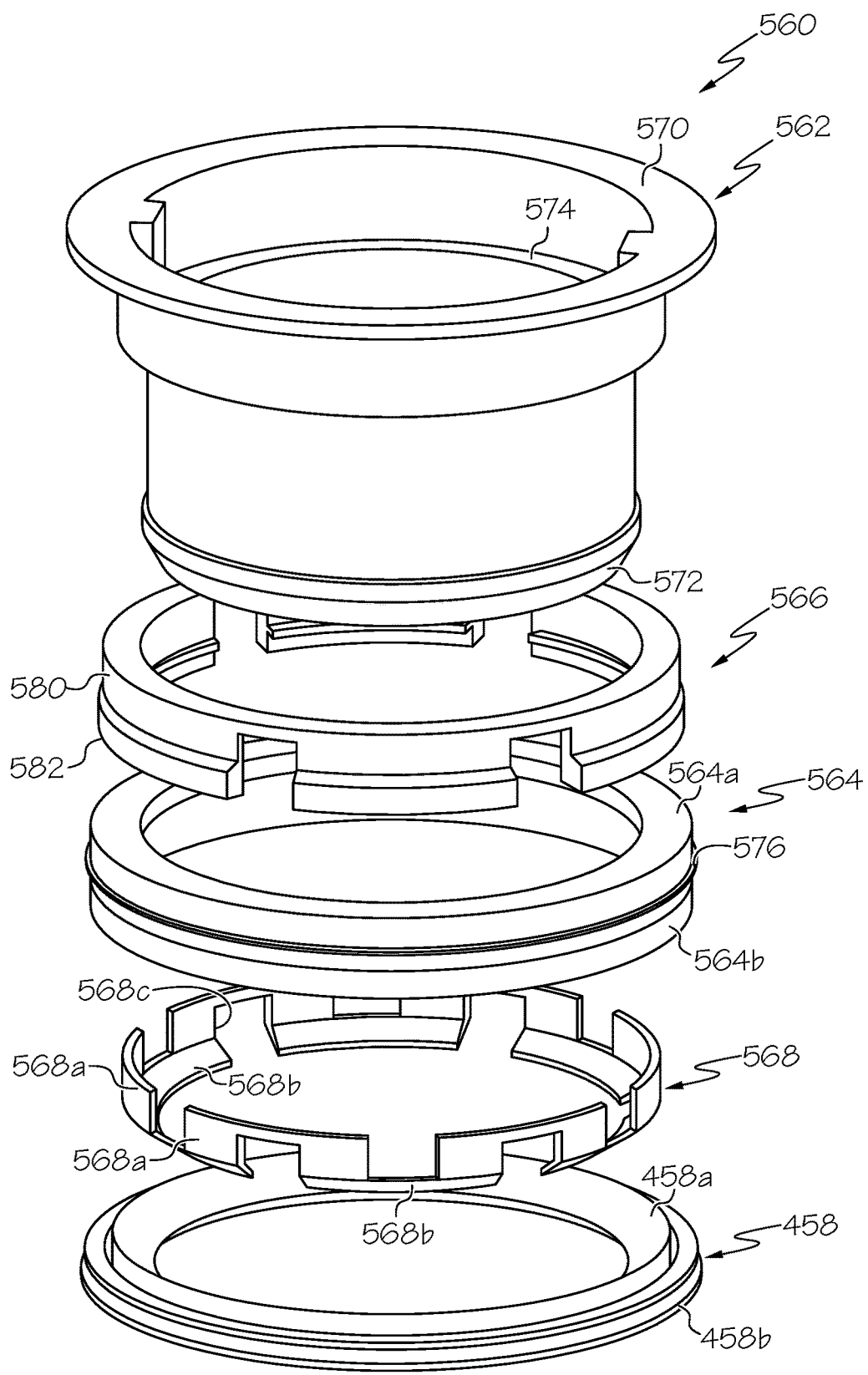
FIG. 10A is an exploded view of one or more rings and a sealing member associated with a housing of the fluid infusion device of FIG. 7.

The retainer ring 566 retains the release ring 562 when the release ring 562 is coupled to the housing 420. With reference to FIG. 8, the retainer ring 566 is substantially annular, and includes a protrusion 580 at a first end, which mates with the tab 572 to retain the release ring 562. With reference to FIGS. 10 and 10A, at a second end, the retainer ring 566 includes one or more tabs 582, which are spaced apart about a perimeter or circumference of the retainer ring 566. The tabs 582 cooperate with an end of the second leg 564b of the compliance ring 564, and generally support the compliance ring 564 within the housing 420. The retainer ring 566 includes a body section, defined between the first end and the second end, which extends along an axis substantially parallel with the longitudinal axis 421. The retainer ring 566 can be composed of any suitable material, and in one example, the retainer ring 566 is composed of a polymeric material, including, but not limited to, polyurethane thermoplastic material. It should be noted, however, that the retainer ring 566 can also be composed of a metal or a ceramic material, if desired. The retainer ring 566 can be molded as one piece, through a suitable forming operation.

With reference to FIG. 8, the anchoring ring 568 secures or locks the connector system 470 within the housing 420. With reference to FIG. 10A, the anchoring ring 568 defines a plurality of elbow-shaped portions, which are interconnected in a pattern to define a circumferential ring. The anchoring ring 568 can include a plurality of first legs 568a angled relative to a respective one of a plurality of second legs 568b by about 90 degrees to about 160 degrees, and in one example, the respective first leg 568a is angled relative to the respective second leg 568b by about 135 degrees. Generally, a respective one of the plurality of second legs 568b is coupled to two of the plurality of first legs 568a, such that a slot 568c is defined between adjacent portions of the second leg 568b. Thus, the anchoring ring 568 also defines a plurality of slots 568c. In addition, the anchoring ring 568 defines a plurality of slots 568d, which are formed about a perimeter or circumference of the anchoring ring 568 to define the plurality of first legs 568a.

Generally, with reference to FIG. 8, each of the first legs 568a and the second legs 568b have substantially the same length, and each extend about a perimeter or circumference of the first body section 500 when the first body section 500 is coupled to the housing 420. The first leg 568a generally contacts the body of the retainer ring 566, and is positioned below the protrusion 580. The second leg 568b is adjacent to and contacts the sealing member 458. The anchoring ring 568 can be composed of any suitable material, and in one example, the anchoring ring 568 is composed of a metal material, including, but not limited to, stainless steel. It will be understood, however, that the anchoring ring 568 can be composed of a polymeric material, such as a polycarbonate; and can also be composed of a ceramic material, if desired. The anchoring ring 568 can be formed as one piece, through a suitable forming operation, for example, 3D printing, stamping, etc.

With reference to FIG. 7, with the housing 420 assembled with the power supply 224, the control module 226 and the drive system 228 (FIG. 3), the fluid reservoir system 430 can be coupled to the housing 420. With reference to FIG. 8, the release ring 562, the compliance ring 564, the retainer ring 566, the anchoring ring 568 and the sealing member 458 are all positioned within and coupled to the reservoir chamber 220b of the housing 420. With the fluid reservoir 256 coupled to the housing 420, the set connector system 414 (FIG. 7), with the needle 272 and the tube 210 coupled to the connector system 470, is coupled to the housing 420. In one example, the connector system 470 is inserted into the release ring 562. The contact between the lip 512b and the notch 578 drives the release ring 562 in a direction D3. The downward movement of the release ring 562 causes the second leg 568b to engage the tab 572 of the release ring 562, thereby securely coupling the connector system 470 to the housing 420.

With reference to FIG. 7, with the set connector system 414 fixedly coupled or secured to the housing 220, the fluid flow path for the fluid 265 out of the fluid reservoir 256 is defined. With the set connector system 414 coupled to the fluid reservoir 256 (FIG. 3), one or more control signals from the control module 226 can drive the motor 234, thereby rotating the drive screw 238, which results in the linear translation of the slide 240 (FIG. 3). The advancement of the slide 240 into the fluid reservoir 256 moves the stopper 262, causing the fluid 265 to flow from the fluid reservoir 256 through the fluid flow path defined by the set connector system 414.

As the fluid flows through the needle 272, the fluid passes through the filter 324. Any gas (e.g. air bubbles) within the fluid is trapped by the filter 324. As the reservoir chamber 420b is generally operating under a pressure, which is greater than a pressure in the ambient environment exterior to and surrounding the housing 420, the trapped gas is drawn through the filter 324 into the first conduit 340 and the second conduit 342. The gas trapped by the filter 324 flows from the filter 324 into the first inlet 344a of the first conduit passage 344 of each of the first conduit 340 and the second conduit 342. The pressure of the gas in the first conduit passage 344 causes the first valve 352 to open, thereby exhausting the gas from the first conduit passage 344 into the second conduit passage 346. From the second conduit passage 346, the gas flows to the third conduit passage 348 and exits into the bore 532 of the respective outlet 530. The pressure of the gas at the respective outlet 530 causes the second valve 550 to open, allowing the trapped gas to flow from the vent subsystem 518 through the conduit 536, where the trapped gas is exhausted into the ambient environment exterior to and surrounding the housing 420.

In order to remove the connector system 470, for example, to replace an empty fluid reservoir 256, with reference to FIG. 8, a second force can be applied in the direction D3 to cause the anchoring ring 568 to be pushed outward toward the retainer ring 566 and the compliance ring 564, thereby disengaging the anchoring ring 568 from the tab 572 of the release ring 562. With the anchoring ring 568 disengaged, the connector system 470 can be removed from the housing 420.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device, comprising:
   a housing having a first chamber that receives a removable fluid reservoir, the fluid reservoir having a first end and a second end; and
   a connector system having a first body section coupled to a second body section, the first body section defining a bore in communication with a chamber and a counterbore of the second body section, the counterbore of the second body section receives and mates with the second end of the fluid reservoir to define a fluid flow path from the fluid reservoir, the second body section received within the first chamber to retain the fluid reservoir within the housing, the chamber of the second body section in fluid communication with a vent subsystem defined through the second body section, the vent subsystem terminating in an outlet, and the vent subsystem directs gas in the fluid flow path through the second body section to the outlet, wherein the vent subsystem comprises a plurality of conduit passages, with at least one valve fluidly coupled between one of the plurality of conduit passages and another of the plurality of conduit passages, the at least one valve comprises a one-way valve, the at least one valve is downstream from the chamber of the second body section and the chamber of the second body section includes a filter in communication with the fluid flow path that filters the gas from fluid in the fluid flow path to remove the gas that is trapped in the fluid in the fluid flow path.

2. The fluid infusion device of claim 1, wherein the chamber is annular, and includes a filter in communication with the fluid flow path that filters the gas from fluid in the fluid flow path to remove the gas that is trapped in the fluid in the fluid flow path.

3. The fluid infusion device of claim 1, wherein the outlet is defined within a thread that at least partially surrounds the second body section.

4. The fluid infusion device of claim 1, wherein the outlet is in fluid communication with a conduit defined in the housing associated with the fluid infusion device to vent the gas to an ambient environment external to the housing.

5. The fluid infusion device of claim 4, wherein the conduit includes a one-way valve that inhibits the flow of fluids into the housing.

6. The fluid infusion device of claim 1, wherein the housing has a first chamber and a second chamber, and the outlet is in fluid communication with the second chamber to vent the gas to the second chamber.

7. The fluid infusion device of claim 1, further comprising a lock that at least partially surrounds a portion of the connector system to securely couple the connector system to the housing associated with the fluid infusion device, and the second body section includes a lock receptacle that receives a portion of the lock to securely couple the connector system to the housing.

8. The fluid infusion device of claim 7, wherein the lock is slidably coupled to the housing, the lock is slidable relative to the housing between a first, locked position in which the connector system is secured to the housing and a second, release position in which the connector system is removable from the housing, and the lock is biased into the first, locked position.

9. The fluid infusion device of claim 1, further comprising at least one ring disposed within a housing of the fluid infusion device that cooperates with the connector system to securely couple the connector system to the housing.

10. The fluid infusion device of claim 9, wherein the at least one ring comprises a plurality of rings, with one of the plurality of rings coupled to the connector system and movable in a direction parallel to a longitudinal axis of the housing and relative to the other of the plurality of rings to securely couple the connector system to the housing.

11. A fluid infusion device, comprising:
a housing defining a first chamber that receives a fluid reservoir and a second chamber adjacent to the first chamber, the first chamber defining at least one chamber thread and the fluid reservoir having a first end and an opposite second end;
a set connector system for venting a gas from the fluid reservoir, the set connector system including a connector system having a first body section coupled to a second body section, the first body section defining a bore, the second body section including a counterbore that receives and mates with the second end of the fluid reservoir, the second body section received within the first chamber to retain the fluid reservoir within the housing, the bore of the first body section and the counterbore of the second body section cooperate to define a fluid flow path from the fluid reservoir, the second body section defining at least one thread that mates with the at least one chamber thread, the second body section including a vent subsystem in communication with the fluid flow path that terminates in an outlet defined within the at least one thread, the vent subsystem directs gas in the fluid flow path to the outlet, and the second body section defines a chamber in fluid communication with the bore of the first body section and the counterbore, the chamber is in communication with the vent subsystem and the chamber includes a filter in communication with the fluid flow path that filters the gas from fluid in the fluid flow path to remove the gas that is trapped in the fluid in the fluid flow path; and
a lock coupled to the housing that at least partially surrounds a portion of the connector system, the lock slidable relative to the housing between a first, locked position in which the connector system is secured to the housing and a second, release position in which the connector system is removable from the housing,
wherein the second body section includes a lock receptacle that receives a portion of the lock to securely couple the connector system to the housing and the vent subsystem comprises a plurality of conduit passages, with at least one valve fluidly coupled between one of the plurality of conduit passages and another of the plurality of conduit passages, the at least one valve comprises a one-way valve and the at least one valve is downstream from the chamber that includes the filter.

12. The fluid infusion device of claim 11, wherein the at least one thread at least partially surrounds the second body section.

13. The fluid infusion device of claim 11, wherein the outlet is in fluid communication with the second chamber to vent the gas to the second chamber.

\* \* \* \* \*